(12) United States Patent
Miller et al.

(10) Patent No.: US 9,138,260 B2
(45) Date of Patent: Sep. 22, 2015

(54) MULTI-LOCKING EXTERNAL FIXATION CLAMP

(75) Inventors: Stephen T. Miller, Scotts Valley, CA (US); Michael W. Mullaney, Kinnelon, NJ (US)

(73) Assignee: Zimmer, Inc., Warsaw, IN (US)

( * ) Notice: Subject to any disclaimer, the term of this patent is extended or adjusted under 35 U.S.C. 154(b) by 309 days.

(21) Appl. No.: 13/175,343

(22) Filed: Jul. 1, 2011

(65) Prior Publication Data

US 2012/0004659 A1    Jan. 5, 2012

Related U.S. Application Data

(60) Provisional application No. 61/360,890, filed on Jul. 1, 2010.

(51) Int. Cl.
*A61B 17/70* (2006.01)
*A61B 17/64* (2006.01)
*A61B 17/60* (2006.01)

(52) U.S. Cl.
CPC .............. *A61B 17/6466* (2013.01); *A61B 17/60* (2013.01)

(58) Field of Classification Search
USPC .............. 403/85, 91–108; 606/53–60; 269/43, 269/45, 95, 6, 3, 143, 249
See application file for complete search history.

(56) References Cited

U.S. PATENT DOCUMENTS

| | | | |
|---|---|---|---|
| 1,706,215 A | | 3/1929 | Davidson |
| 2,370,733 A | * | 3/1945 | Jones .............................. 30/90.7 |
| 2,627,774 A | * | 2/1953 | Walter ............................. 81/368 |
| 2,705,603 A | | 4/1955 | Bitz et al. |
| 2,865,240 A | * | 12/1958 | Kniser .............................. 269/6 |
| 2,940,345 A | * | 6/1960 | Farina ............................. 81/380 |

(Continued)

FOREIGN PATENT DOCUMENTS

| CN | 103260535 A | 8/2013 |
|---|---|---|
| DE | 2430234 | 1/1975 |

(Continued)

OTHER PUBLICATIONS

European Patent Office, International Search Report and Written Opinion dated Oct. 13, 2011 for Application No. PCT/US2011/042813, 11 pages.

(Continued)

*Primary Examiner* — Jan Christopher Merene
*Assistant Examiner* — Steven Cotroneo
(74) *Attorney, Agent, or Firm* — Schwegman Lundberg & Woessner, P.A.

(57) ABSTRACT

A clamping device for attaching to an external fixation element of an external fixation system includes a first jaw having an inner surface and an outer surface and includes a second jaw having an inner surface and an outer surface, with the inner surface of the first jaw and the inner surface of the second jaw together forming a passage configured to receive the external fixation element of the external fixation system. A locking system is engageable with the first and the second jaws. A portion of the locking system is moveable relative to the first and the second jaws between a first position where the locking arrangement is configured to prevent release of the external fixation element having a first size from between the first jaw and the second jaw and a second position where the locking arrangement is configured to prevent release of the external fixation element having a second size from between the first jaw and the second jaw.

16 Claims, 22 Drawing Sheets

(56) References Cited

U.S. PATENT DOCUMENTS

| | | |
|---|---|---|
| 3,044,512 A | 7/1962 | Jones |
| 3,154,331 A | 10/1964 | Engelhardt |
| 3,354,755 A * | 11/1967 | Legrande ................ 81/314 |
| 3,373,465 A | 3/1968 | Johnson et al. |
| 3,406,987 A | 10/1968 | Hunder et al. |
| 4,037,978 A | 7/1977 | Connelly |
| 4,115,966 A | 9/1978 | DeLee |
| 4,312,488 A | 1/1982 | Pierron |
| 4,388,747 A | 6/1983 | Plummer |
| 4,483,334 A | 11/1984 | Murray |
| 4,620,533 A * | 11/1986 | Mears ..................... 606/54 |
| 4,653,481 A | 3/1987 | Howland et al. |
| 4,662,365 A | 5/1987 | Gotzen et al. |
| 4,700,437 A * | 10/1987 | Hoshino ................... 24/456 |
| D295,725 S | 5/1988 | Shioda |
| 4,817,897 A | 4/1989 | Kreusel |
| 5,312,405 A | 5/1994 | Korotko et al. |
| 5,427,465 A | 6/1995 | Sato |
| 5,662,648 A | 9/1997 | Faccioli et al. |
| 5,676,029 A * | 10/1997 | Putsch ..................... 81/412 |
| 5,683,389 A | 11/1997 | Orsak |
| 5,709,681 A | 1/1998 | Pennig |
| 5,727,899 A | 3/1998 | Dobrovolny |
| 5,741,252 A | 4/1998 | Mazzio et al. |
| 5,746,741 A | 5/1998 | Kraus et al. |
| 5,752,954 A | 5/1998 | Mata et al. |
| 5,800,548 A | 9/1998 | Martin et al. |
| 5,827,282 A | 10/1998 | Pennig |
| 5,860,728 A | 1/1999 | Maglica |
| 5,891,144 A | 4/1999 | Mata et al. |
| 5,976,141 A | 11/1999 | Haag et al. |
| 6,022,348 A | 2/2000 | Spitzer |
| 6,080,153 A * | 6/2000 | Mata et al. ................ 606/54 |
| 6,102,911 A | 8/2000 | Faccioli et al. |
| 6,217,577 B1 | 4/2001 | Hofmann |
| 6,264,396 B1 | 7/2001 | Dobrovolny |
| 6,277,069 B1 | 8/2001 | Gray |
| 6,376,775 B1 | 4/2002 | Leijon et al. |
| 6,386,786 B1 | 5/2002 | Perlman et al. |
| 6,409,729 B1 | 6/2002 | Martinelli |
| 6,500,177 B1 | 12/2002 | Martinelli et al. |
| 6,637,082 B1 | 10/2003 | Chang |
| 6,652,523 B1 | 11/2003 | Evrard et al. |
| 6,702,814 B2 | 3/2004 | Walulik et al. |
| 6,716,212 B1 | 4/2004 | Pickens |
| 6,736,775 B2 | 5/2004 | Phillips |
| 6,887,197 B2 | 5/2005 | Phillips |
| 7,004,943 B2 | 2/2006 | Ferrante et al. |
| 7,048,735 B2 | 5/2006 | Ferrante et al. |
| 7,222,558 B2 * | 5/2007 | Schmitt et al. .............. 81/411 |
| 7,241,071 B2 * | 7/2007 | Carraher et al. ............ 403/164 |
| 7,241,074 B2 | 7/2007 | Thomke et al. |
| 7,261,713 B2 | 8/2007 | Langmaid |
| 7,314,331 B1 | 1/2008 | Koros et al. |
| 7,320,556 B2 | 1/2008 | Vagn-Erik |
| 7,473,223 B2 | 1/2009 | Fetzer |
| 7,491,008 B2 | 2/2009 | Thomke et al. |
| 7,527,626 B2 | 5/2009 | Lutz et al. |
| 7,562,855 B2 | 7/2009 | Oetlinger |
| 7,588,537 B2 | 9/2009 | Bass |
| 7,707,694 B2 * | 5/2010 | Holzer et al. ............... 24/68 SK |
| 7,708,736 B2 | 5/2010 | Mullaney |
| 7,744,632 B2 | 6/2010 | Usher |
| 7,887,537 B2 | 2/2011 | Ferrante et al. |
| 7,931,650 B2 | 4/2011 | Winquist et al. |
| 7,938,829 B2 | 5/2011 | Mullaney |
| 2001/0004432 A1 | 6/2001 | Pfister |
| 2002/0037193 A1 | 3/2002 | Gibbons et al. |
| 2002/0042613 A1 | 4/2002 | Mata |
| 2002/0061225 A1 | 5/2002 | Boucher et al. |
| 2002/0165543 A1 | 11/2002 | Winquist et al. |
| 2003/0149429 A1 * | 8/2003 | Ferrante et al. .............. 606/59 |
| 2004/0044344 A1 | 3/2004 | Winquist et al. |
| 2005/0113831 A1 | 5/2005 | Franck et al. |
| 2006/0017566 A1 | 1/2006 | Gauvreau et al. |
| 2006/0039750 A1 | 2/2006 | Thomke |
| 2006/0229602 A1 | 10/2006 | Olsen |
| 2006/0229603 A1 | 10/2006 | Olsen |
| 2006/0255521 A1 | 11/2006 | Brunner |
| 2006/0271045 A1 | 11/2006 | Hubbard et al. |
| 2006/0287652 A1 | 12/2006 | Lessig et al. |
| 2007/0038217 A1 | 2/2007 | Brown et al. |
| 2007/0049932 A1 | 3/2007 | Richelsoph et al. |
| 2007/0198012 A1 | 8/2007 | Thomke et al. |
| 2007/0293860 A1 | 12/2007 | Oesch |
| 2008/0065068 A1 | 3/2008 | Thomke et al. |
| 2008/0215053 A1 | 9/2008 | Thomke et al. |
| 2009/0036891 A1 | 2/2009 | Brown et al. |
| 2009/0088751 A1 * | 4/2009 | Mullaney ................. 606/59 |
| 2009/0148232 A1 * | 6/2009 | Thomke et al. ............ 403/373 |
| 2009/0299368 A1 | 12/2009 | Bauer |
| 2011/0098706 A1 | 4/2011 | Mullaney |
| 2011/0098707 A1 | 4/2011 | Mullaney |
| 2011/0172663 A1 | 7/2011 | Mullaney |
| 2012/0089142 A1 | 4/2012 | Mullaney et al. |
| 2012/0095462 A1 | 4/2012 | Miller |

FOREIGN PATENT DOCUMENTS

| | | |
|---|---|---|
| EP | 1820461 | 8/2007 |
| EP | 2294994 | 3/2011 |
| JP | 2013530775 A | 8/2013 |
| WO | WO-89/05126 | 6/1989 |
| WO | WO9011055 | 10/1990 |
| WO | WO9212683 | 8/1992 |
| WO | WO9851227 | 11/1998 |
| WO | WO9925264 | 5/1999 |
| WO | WO-03/065911 | 8/2003 |
| WO | WO-2009/004347 | 1/2009 |
| WO | WO-2012003455 | 1/2012 |

OTHER PUBLICATIONS

European Patent Office, International Search Report and Written Opinion mailed Mar. 28, 2012, Application No. PCT/US2011/963985, 10 pages.

European Patent Office, International Search Report and Written Opinion mailed Mar. 20, 2012, Application No. PCT/US2011/059303, 13 pages.

European Patent Office, International Search Report and Written Opinion mailed Apr. 10, 2012, Application No. PCT/US2011/063976, 8 pages.

European Patent Office, International Search Report and Written Opinion mailed Jan. 9, 2012, Application No. PCT/US2011/055907, 9 pages.

Swiss Patent Office, Office Action dated Dec. 16, 1991, Application No. 03 891/90-6, 34 pages.

"European Application Serial No. 11730540.9, Office Action mailed Mar. 13, 2013", 2 pgs.

"International Application U.S. Appl. No. PCT/US2011/042813, International Preliminary Report on Patentability mailed Jan. 8, 2013", 6 pgs.

"European Application Serial No. 11730540.9, Examination Notification Art. 94(3) mailed Dec. 11, 2013", 3 pgs.

"Japanese Application Serial No. 2013-518761, Office Action mailed Dec. 10, 2013", (W/ English Translation), 12 pgs.

"European Application Serial No. 11730540.9, Examination Notification Art. 94(3) mailed May 20, 2014", 5 pgs.

"Japanese Application U.S. Appl. No. 2013-518761, Response filed Mar. 10, 2014 to Office Action mailed Dec. 10, 2013", (W/ English Translation), 17 pgs.

* cited by examiner

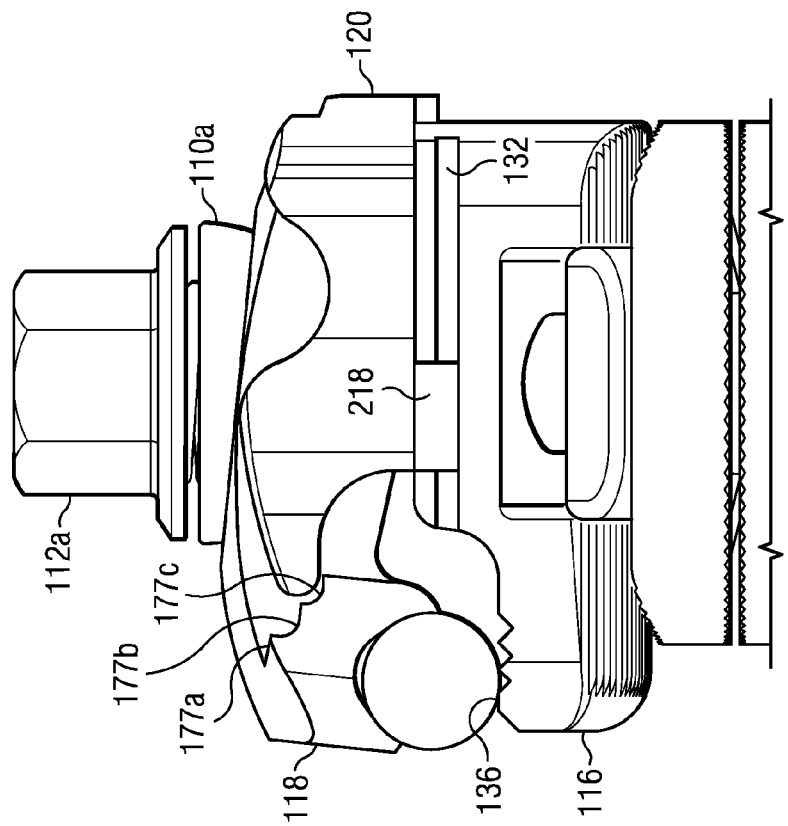
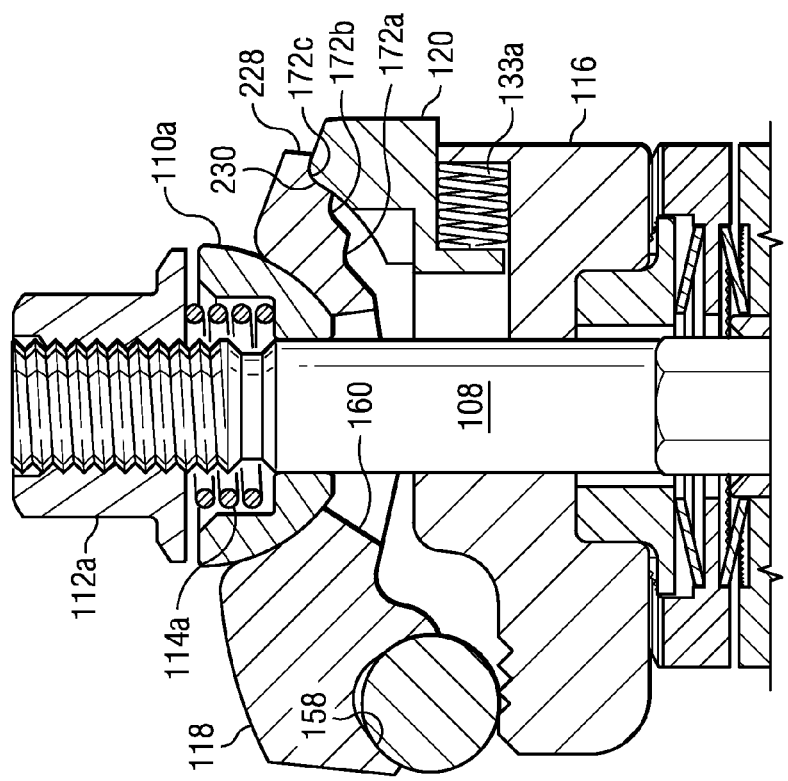
Fig. 10B
Fig. 10A

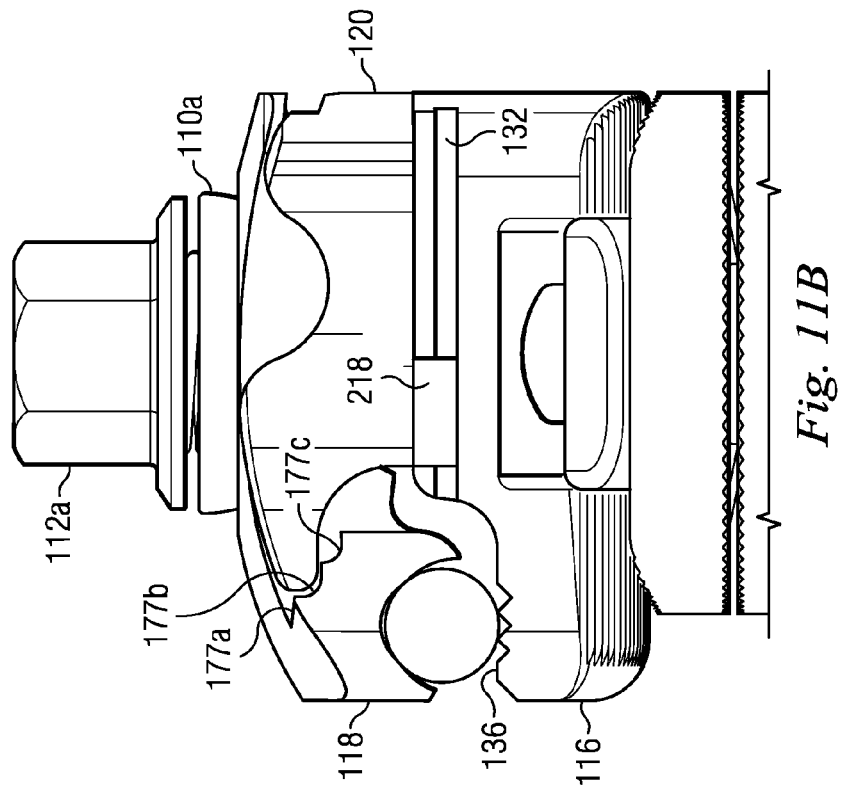
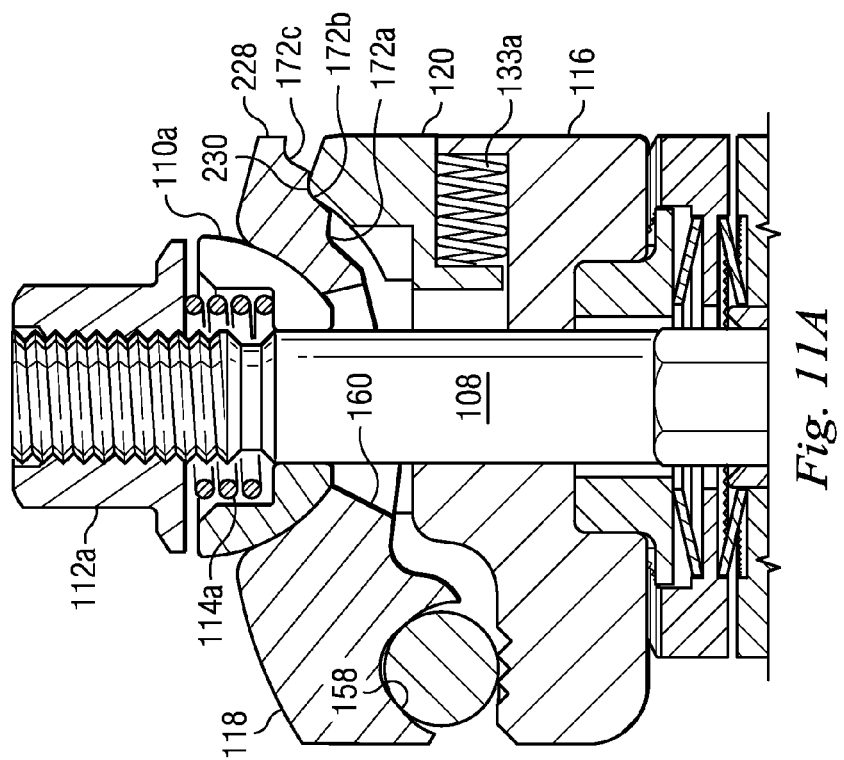

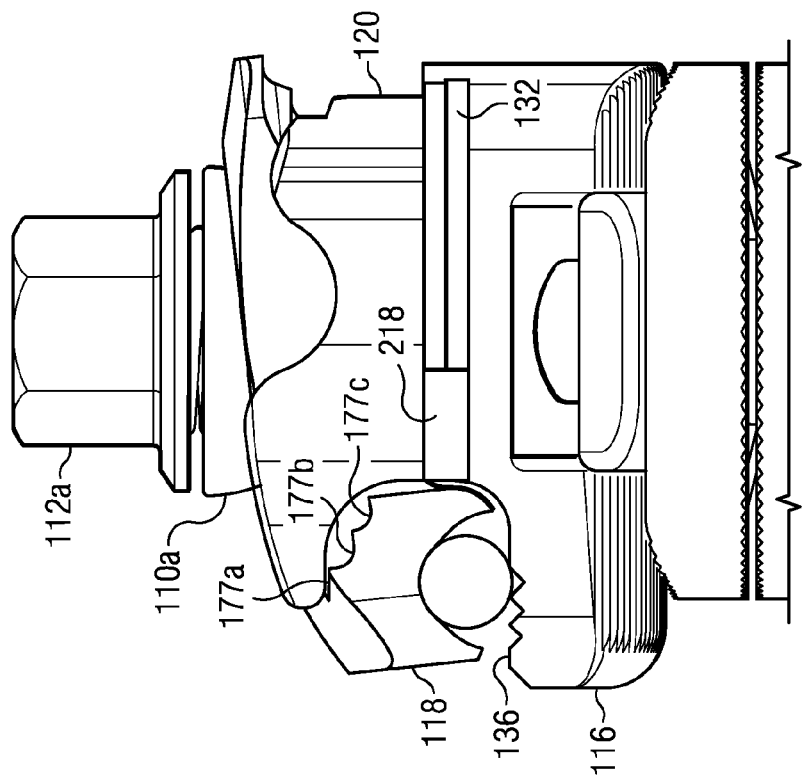
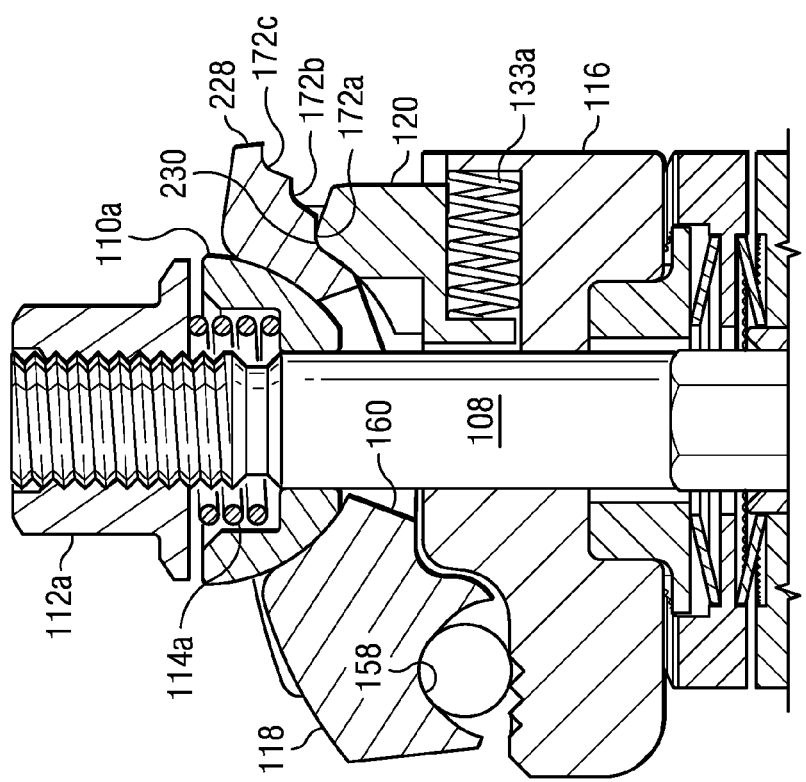

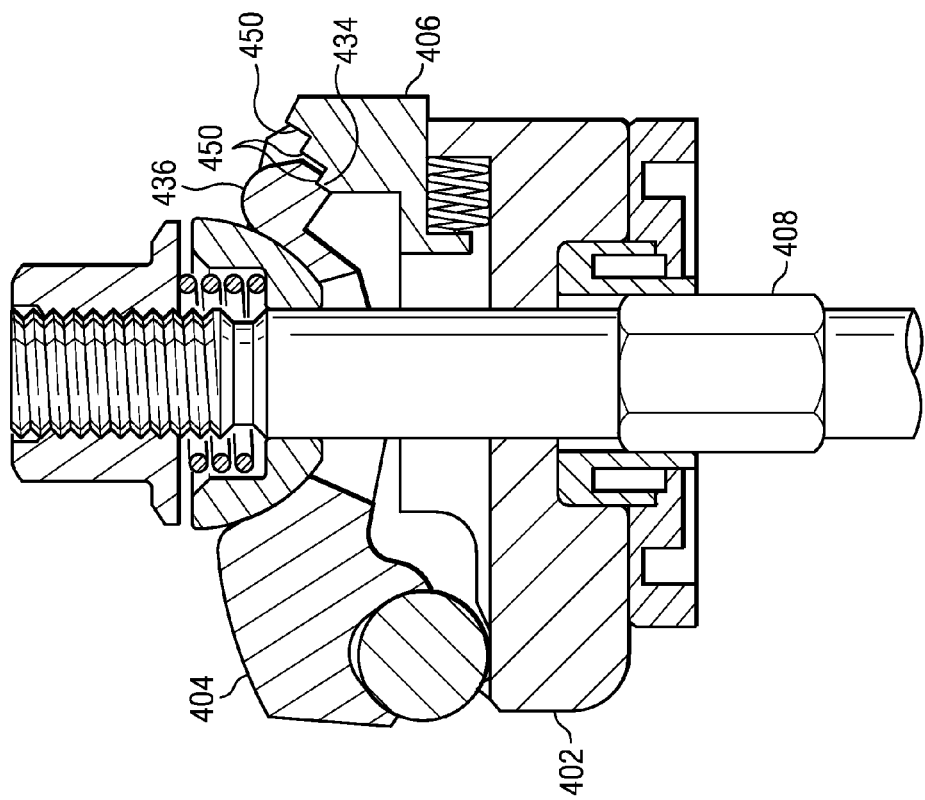
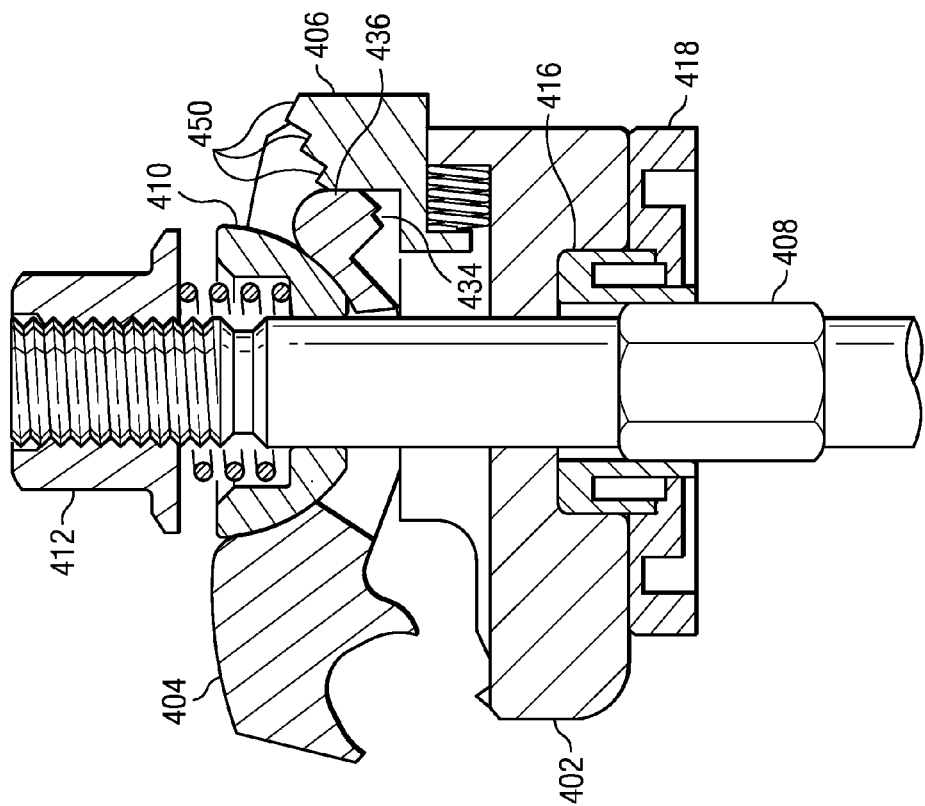

MULTI-LOCKING EXTERNAL FIXATION CLAMP

PRIORITY INFORMATION

This application claims priority to U.S. Provisional Patent Application No. 61/360,890, filed Jul. 1, 2010, which is incorporated herein in its entirety.

FIELD OF THE INVENTION

The present disclosure is directed to external fixation systems for stabilizing bone fragments.

BACKGROUND

External fixation systems use bone pins or wires to stabilize bone segments. These pins or wires are held in space relative to each other by a fixation frame. The frame can be made up of rings, struts, bars or other structural members. The simplest frame is usually made up of bars (sometimes referred to as rods). To hold the bars to each other and to the fixation elements, typically a clamp is engaged to two or more elements. Clamps may also be employed to hold bars to rings, pins to rings, struts to rings, etc.

The user typically constructs the external fixation system by placing the pins into the bone and assembling the frame into the approximate shape needed, then adjusting the position of the bone to get the bone fragments in their proper anatomic location. Then the frame is locked into place by tightening the clamps and other adjustment means.

U.S. Pat. No. 5,752,954 to Mata describes a clamp used to create a frame where the bars are snapped into the clamp. The clamp is constructed of two jaws, each with opposing channels the relative shape of half of the element they are grabbing (such as a bar or pin). The jaws are biased towards each other along the clamping axis by a spring element. When the bar or pin is snapped into the jaw, the biasing element holds the jaws against the bar or pin. This makes assembly easy, but a common complaint is that the jaws can also allow for the bar or pin to pop out when the assembly is being adjusted to the appropriate position.

U.S. Pat. No. 7,004,943 to Ferrante describes a clamp mechanism with two jaws that slide relative to each other perpendicular to the clamping axis. The direction of opening of the jaws is such that force applied by the bar or pin against the jaw does not cause the jaw to open up, which reduces the likelihood of pop-out.

Both of these devices as described, and other similar devices, have the jaws sized to match the component that they lock to, either the bar, pin or another element. One enhancement to the Mata design incorporates a jaw geometry that can clamp against pins of various sizes because the biasing element pushes the jaws together, taking up any slack due to differential sizes. Pop-out can be reduced by adjusting the clamping means to tighten the jaws to nearly full clamping, but making this adjustment is inconvenient for the user.

However, the jaw designs of these prior clamps either do not provide for provisional locking or are limited to provisional locking of only one size of fixation element.

SUMMARY

The present disclosure describes an external fixation system utilizing a clamping device that allows a clamp to connect to different sized fixation system elements through the use of an innovative latch mechanism. The latch mechanism enhances the clamping device so that the user has less need to adjust the fixation system in order to have a stable construct prior to full clamping.

One embodiment of the present disclosure utilizes a latch with a variety of thicknesses so that the back side of the clamp jaws are held apart a different amount depending upon what size of bar or pin is being held or intended to be held in the jaws. Another embodiment of the present disclosure has the latch move to a different position relative to the back of the inner and outer jaws such that the amount the front of the inner and outer jaw can open is restricted based upon the position of the latch. Thus, the width of the opening between the jaws can be controlled using the adjustable latch. Yet an additional embodiment incorporates both options to increase the overall range of locking of the clamp set.

One embodiment of the current disclosure provides a latch that slides relative to the inner and outer jaws to restrict how far they can open relative to each other. The latch and jaws can engage in various locations such that the opening allowed is restricted to a certain amount depending upon the size of the bar or pin engaged in the jaws. A further embodiment incorporates a step in the latch that props the jaws open, making it easier to engage the bar or pin into the jaw. This catch can also be used in conjunction with the wedge type latch described above.

To simplify the description of the clamp element and overall frame construct, the following description will use the terms bars and pins, but other frame elements and fixation means can be substituted.

In one exemplary aspect, the present disclosure is directed to a clamping device for attaching to an external fixation element of an external fixation system. The device includes a first jaw having an inner surface and an outer surface and includes a second jaw having an inner surface and an outer surface. The inner surface of the first jaw and the inner surface of the second jaw together form a passage configured to receive the external fixation element of the external fixation system. A locking system is engageable with the first and the second jaws. A portion of the locking system is moveable relative to the first and the second jaws between a first position where the locking arrangement is configured to prevent release of the external fixation element having a first size from between the first jaw and the second jaw and a second position where the locking arrangement is configured to prevent release of the external fixation element having a second size from between the first jaw and the second jaw.

In one exemplary aspect, the moveable portion of the locking system comprises a wedge configured for selective disposal between the first and the second jaws. In another exemplary aspect, the first jaw comprises first and second engagement surfaces and the moveable portion of the locking system comprises a third engagement surface disposed to selectively engage one of the first and second engagement surfaces on the first jaw.

In another exemplary aspect, the present disclosure is directed to another clamping device for attaching to an external fixation element of an external fixation system. The device includes a first jaw having inner and outer surfaces and a second jaw having inner and outer surfaces. The inner surface of the first jaw and the inner surface of the second jaw together form a passage configured to receive the external fixation element. A locking system is associated with the first jaw and the second jaw and configured to selectively limit separation of the first jaw and the second jaw. The locking system includes a first locking arrangement configured to correspond to a fixation element having a first size with the first locking arrangement being configured to prevent release of the external fixation element having a first size from between the first jaw and the second jaw. The locking system also includes a second locking arrangement configured to correspond to a fixation element having a second size, where the second locking arrangement is configured to prevent release of the external fixation element having a second size from between the first jaw and the second jaw. The first locking arrangement is different than the second locking arrangement and the first size is different than the second size.

In another exemplary aspect, the present disclosure directed to another clamping device that includes a first jaw and includes a second jaw having an inner surface facing the first jaw. The first and second jaws together form a passage for receiving the external fixation element of the external fixation system.

In one aspect, the device includes a locking mechanism having a first portion extendable above a portion of the first jaw and having a second portion extendable below a portion of the second jaw in a manner that prevents separation of the first jaw and the second jaw to prevent release of the external fixation element from between the first jaw and the second jaw.

In another aspect, the device includes a locking mechanism having a first portion extending above the first engagement surface of the first jaw and having a second portion extending below the interfacing surface of the second jaw. A connecting portion rigidly connects the first and second portions in a manner that prevents separation of the first jaw and the second jaw to prevent release of the external fixation element from between the first jaw and the second jaw.

In yet another aspect, device includes a fixation element disposed in the passage between the first and second jaws. A locking mechanism has a first portion extendable above a portion of the fixation element and has a second portion extendable below a portion of the second jaw in a manner that prevents release of the external fixation element from the passage between the first jaw and the second jaw.

In another exemplary aspect, the present disclosure directed to a clamping device for an external fixation system that includes a first jaw and a second jaw having an inner surface facing the first jaw. The first and second jaws together form a passage for receiving a first fixation element of the external fixation system. The device also includes a latching mechanism cooperating with one of the first and second jaws.

In one aspect, the latching mechanism includes a plurality of ridges configured to selectively engage with a ridge on one of the first and second jaws in a manner that limits the rotation of the first and second jaws relative to each other.

In another aspect, the latching mechanism includes a ridge configured to selectively engage with a plurality of ridges on one of the first and second jaws in a manner that limits the rotation of the first and second jaws relative to each other.

In another exemplary aspect, the present disclosure directed to a clamping device for an external fixation system, including a first clamping system, a second clamping system, and a post component extending into the first and second clamping systems. The first clamping system includes a first outer jaw and a first inner jaw having an inner surface facing the outer jaw. The outer and inner jaws together form a passage for receiving a first fixation element of the external fixation system. A locking system is engageable with the first outer and the first inner jaws. A portion of the locking system is moveable relative to the first outer and the first inner jaws between a first position where the locking arrangement is configured to prevent release of an external fixation element having a first size from between the first outer and the first inner jaws and a second position where the locking arrangement is configured to prevent release of an external fixation element having a second size from between the first outer and the first inner jaws. The second clamping system includes a second outer jaw and a second inner jaw having an inner surface facing the second outer jaw. The second outer and second inner jaws together form a second opening for receiving a second fixation element of the external fixation system.

In yet another exemplary aspect, the present disclosure directed to a clamping device for an external fixation system that includes a biasing element, a pivot washer, a first jaw pivotably associated with the pivot washer and being pivotable around the pivot washer between a first position and a second position. A second jaw has an inner surface facing the first jaw. The first and second jaws together form a clamp opening for receiving a fixation element of the external fixation system. When the first jaw is in the first position, the biasing element provides a biasing force on the first jaw that opens the clamp opening. When the first jaw is in the second position, the biasing element provides a biasing force on the first jaw that closes the clamp opening.

BRIEF DESCRIPTION OF THE DRAWINGS

A more complete understanding of the present disclosure and advantages thereof may be acquired by referring to the following description taken in conjunction with the accompanying figures.

FIG. 10A is an illustration of a cross-sectional view of a clamp of FIG. 2 in a first locking condition for a first sized fixation element.

FIG. 10B is an illustration of a plan view of the clamp of 9A in the first locking condition for the first sized fixation element.

FIG. 11A is an illustration of a cross-sectional view of a clamp of FIG. 2 in a second locking condition for a second sized fixation element.

FIG. 11B is an illustration of a plan view of the clamp of 9A in the first locking condition for the second sized fixation element.

FIG. 12A is an illustration of a cross-sectional view of a clamp of FIG. 2 in a third locking condition for a third sized fixation element.

FIG. 12B is an illustration of a plan view of the clamp of 9A in the third locking condition for the third sized fixation element.

FIG. 21 is an illustration of a cross-sectional view of the clamp of FIG. 18 in an open condition in accordance with one exemplary aspect of the present disclosure.

FIG. 22 is an illustration of a cross-sectional view of the clamp of FIG. 18 in a first locking condition for a first sized fixation element.

DETAILED DESCRIPTION

Figure 1:
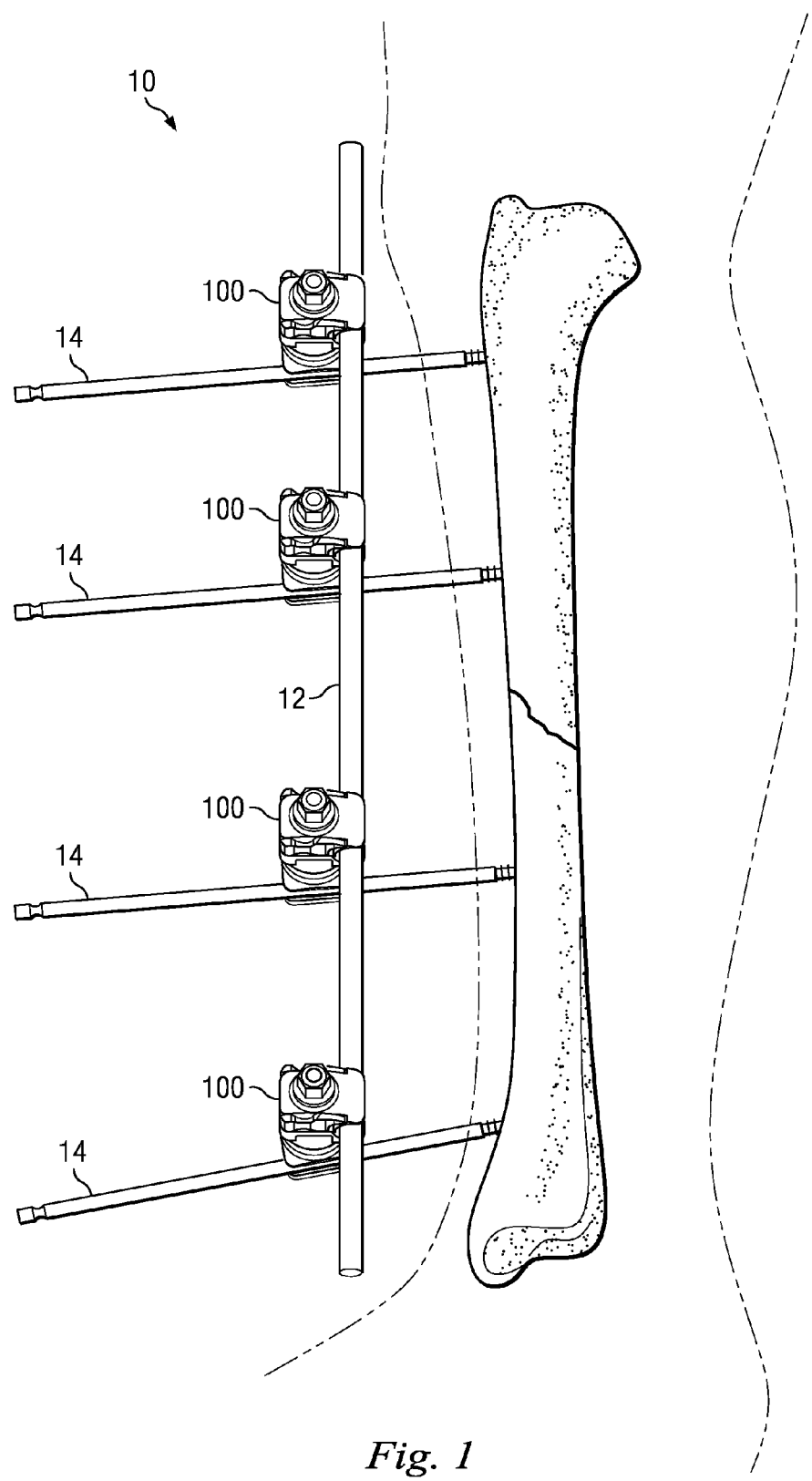
FIG. 1 is an illustration of an exemplary external fixation system in accordance with one exemplary aspect of the present disclosure.

The present disclosure relates generally to the field of external fixation systems, and more particularly to clamping devices for connecting bone pins, wires, rings, struts, bars, rods, or other structural members (referred to collectively as "fixation elements"). For the purposes of promoting an understanding of the principles of the invention, reference will now be made to embodiments or examples illustrated in the drawings, and specific language will be used to describe these examples. It will nevertheless be understood that no limitation of the scope of the invention is thereby intended. Any alteration and/or further modifications in the described embodiments, and any further applications of the principles of these inventions as described herein are contemplated as would normally occur to one skilled in the art to which the disclosure relates.

The external fixation system disclosed herein provides the advantage of being able to receive and secure fixation rods of different sizes into a provisional locking arrangement. To do this, the external fixation system is particularly arranged to receive rods of different sizes, but also includes a latching system with a plurality of engagement features that correspond to different sized rods. When a rod of a particular size is introduced to the clamping device, the clamping device is able to capture the rod in the provisional locking arrangement while reducing the chance that smaller rods may be prematurely removed from the clamp.

In addition, the clamping device disclosed herein is particularly useful for capturing the rod by using a system that latches or interfaces with both upper and lower jaws to mechanically provide a positive lock that limits the separation of the jaws. As such, after a rod is introduced into the clamping system, the latch may be used to positively connect the two jaws so that the rod cannot be removed.

Each clamp of the clamping device itself includes an open position, a provisional locking condition where the bar is unable to be removed but may be rotated or axially displaced, and a fully locked condition, where the fixation system is rigidly fixed on the rod. The nature of the fixation system allows the motion of the rod to displace clamping elements to capture fixation elements and move to the provisional locking condition.

FIG. 1 shows an exemplary external fixation system 10 attached to a patient's fractured tibia. The system 10 includes a rigid bar 12 and plurality of pins 14 drilled into the bone on opposing sides of the fracture. A clamping device 100 connects each pin 14 to the bar 12 for rigid fixation and traction. Each pin 14 is received into a clamping device 100 by inserting the pin 14 between open inner and outer jaws of a fixator clamp of the clamping device 100 as is described further below. In some embodiments, inserting the pin 14 triggers the fixator clamp to change from an open position to a provisionally locked position about the pin 14. The provisionally locked position is one that may be influenced in part by the size of the fixation element. In this position, the fixator clamp can be rotated about the pin 14 and may be axially displaced along the pin 14. In addition, it may rotate about a longitudinal axis of the clamping device, and it may pitch up or down around the cylindrical axis of a saddle element, but the jaws maintain the pin in the clamp. Once the pins 14 are set, the bar 12 is introduced into another fixator clamp on the clamping device 100, forming a frame for the system 10. In some embodiments, as with the pins 14, inserting the bar 12 triggers the fixator clamp to change from an open position to a provisionally locked position. As remaining pins 14 are connected to the bar 12 using the clamping device 100, the clamping devices may be adjusted to provide angulation and orientation necessary to align the bone for healing. Additional bar-to-bar fixation components and/or bar-to-pin fixation components may be added to expand and connect the frame as required. Once properly created, the frame may be locked by changing the clamp from the provisionally locked condition to the locked condition.

FIGS. 2-5 show an exemplary embodiment of a clamping device 100 according to one exemplary aspect of the present disclosure. For convenience in FIGS. 2-5, similar components are labeled with the same reference number, but are distinguished by a suffix, with the suffix "a" identifying components of the first or top clamp 102 and the suffix "b" identifying components of the bottom or second clamp 104.

The exemplary clamping device 100 includes a bar clamp 102, a pin clamp 104, and a saddle assembly 106 disposed therebetween. Each clamp 102, 104 independently receives and secures a bar, pin or other fixation element. Other embodiments of the clamping device 100 include two bar clamps or two pin clamps. Yet other embodiments include only a single clamp on one end, with a multi-clamp set or other arrangement on the other end.

Figure 2:
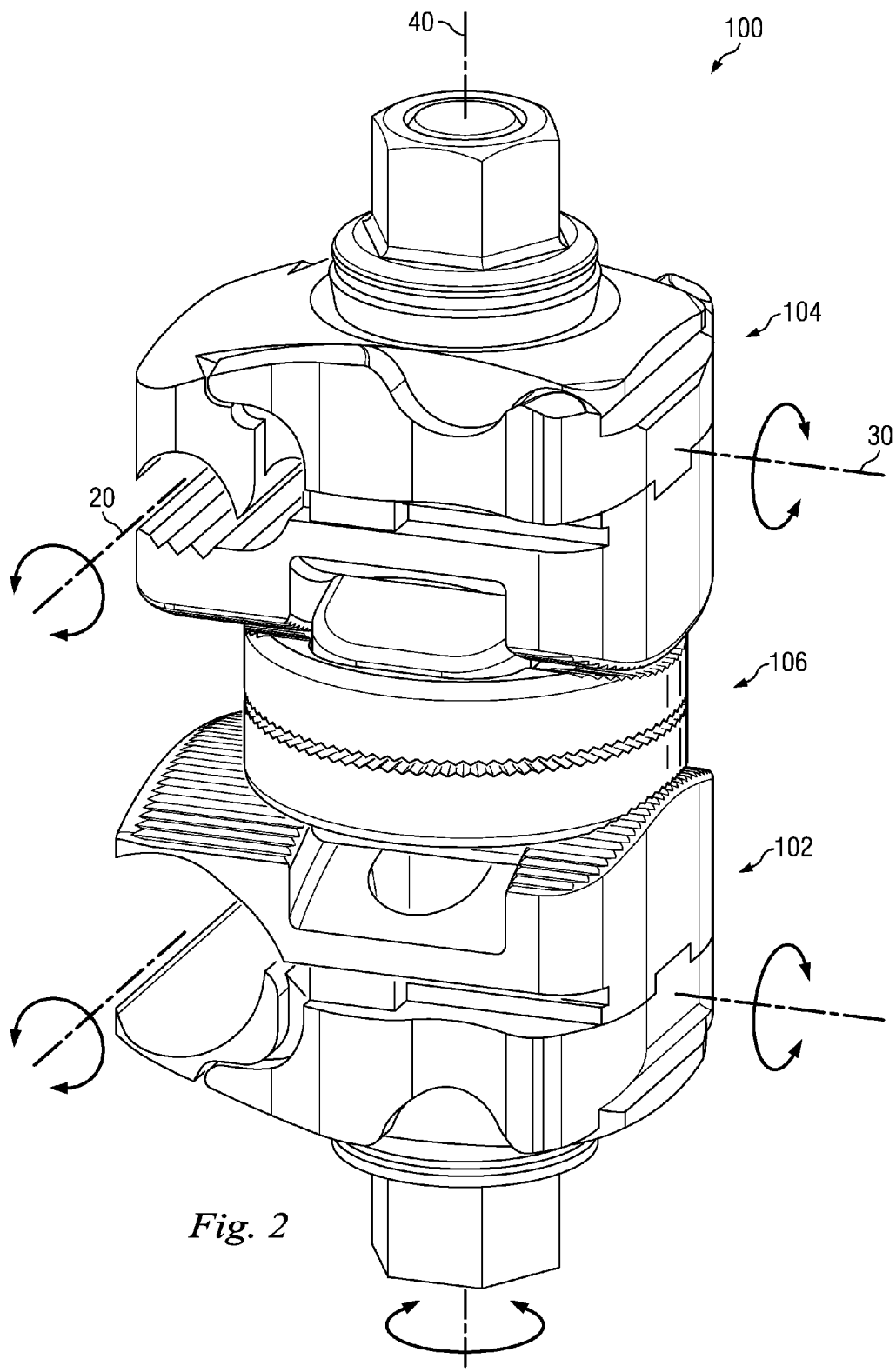
FIG. 2 is an illustration of a clamping device from the external fixation system of FIG. 1 in accordance with one exemplary aspect of the present disclosure.

Each clamp 102, 104 of the clamping device 100 provides multiple degrees of freedom. FIG. 2 shows the degrees of freedom as a roll axis 20, a pitch axis 30, and a yaw axis 40 in the upper and lower clamps 102, 104. The roll axis 20 is the axis of a bar within the clamps and about which the clamping device 100 rotates. The pitch axis 30 is the axis about which the outer and inner jaws rotate relative to the saddle assembly 106 and relative to the opposing clamp. The yaw axis 40 is defined by a stud (described below) and about which one of the clamps 102, 104 can rotate relative to the other.

Figure 3:
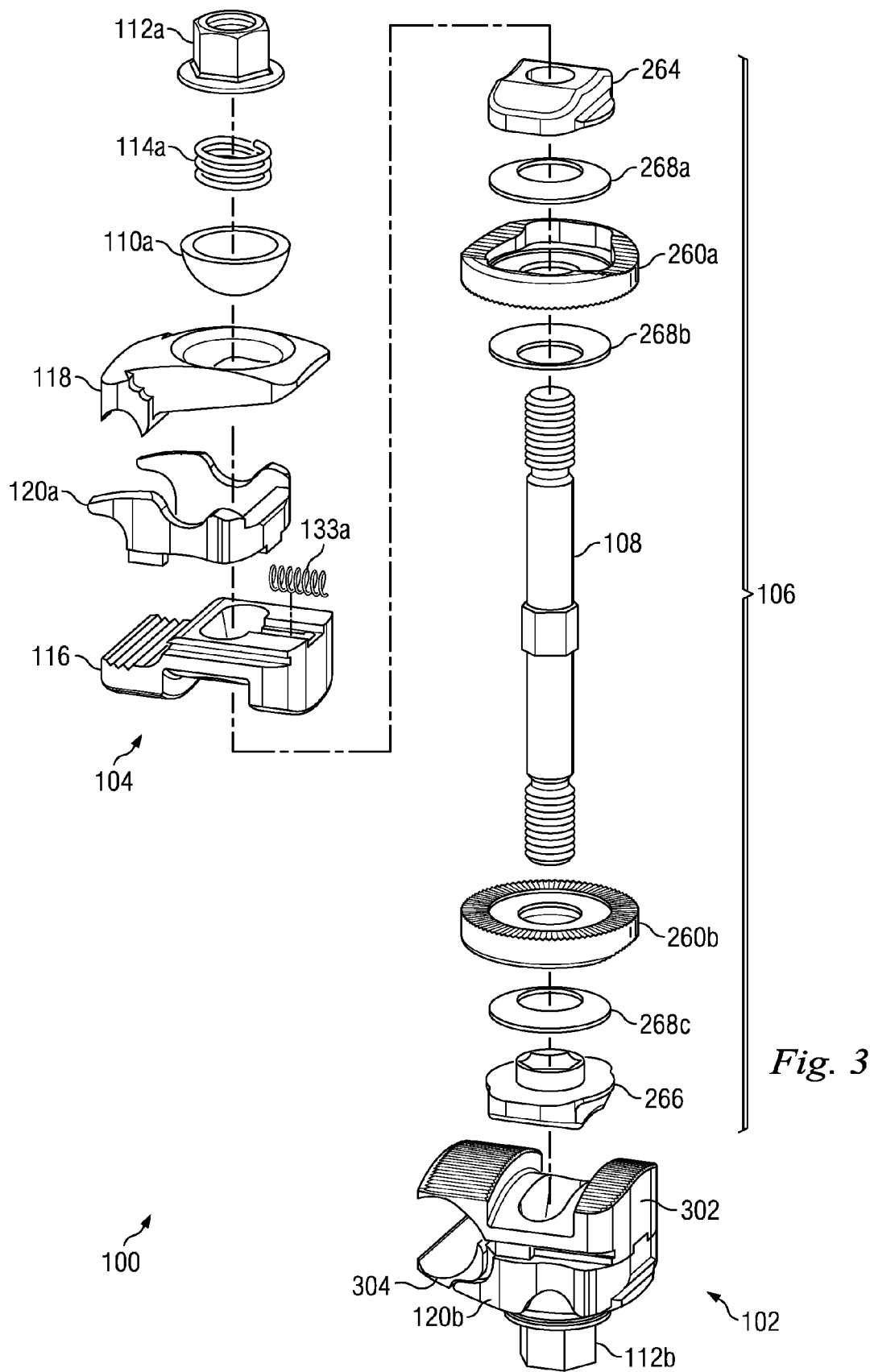
FIG. 3 is an illustration of a partial exploded view of the clamping device of FIG. 2.
Figure 4:
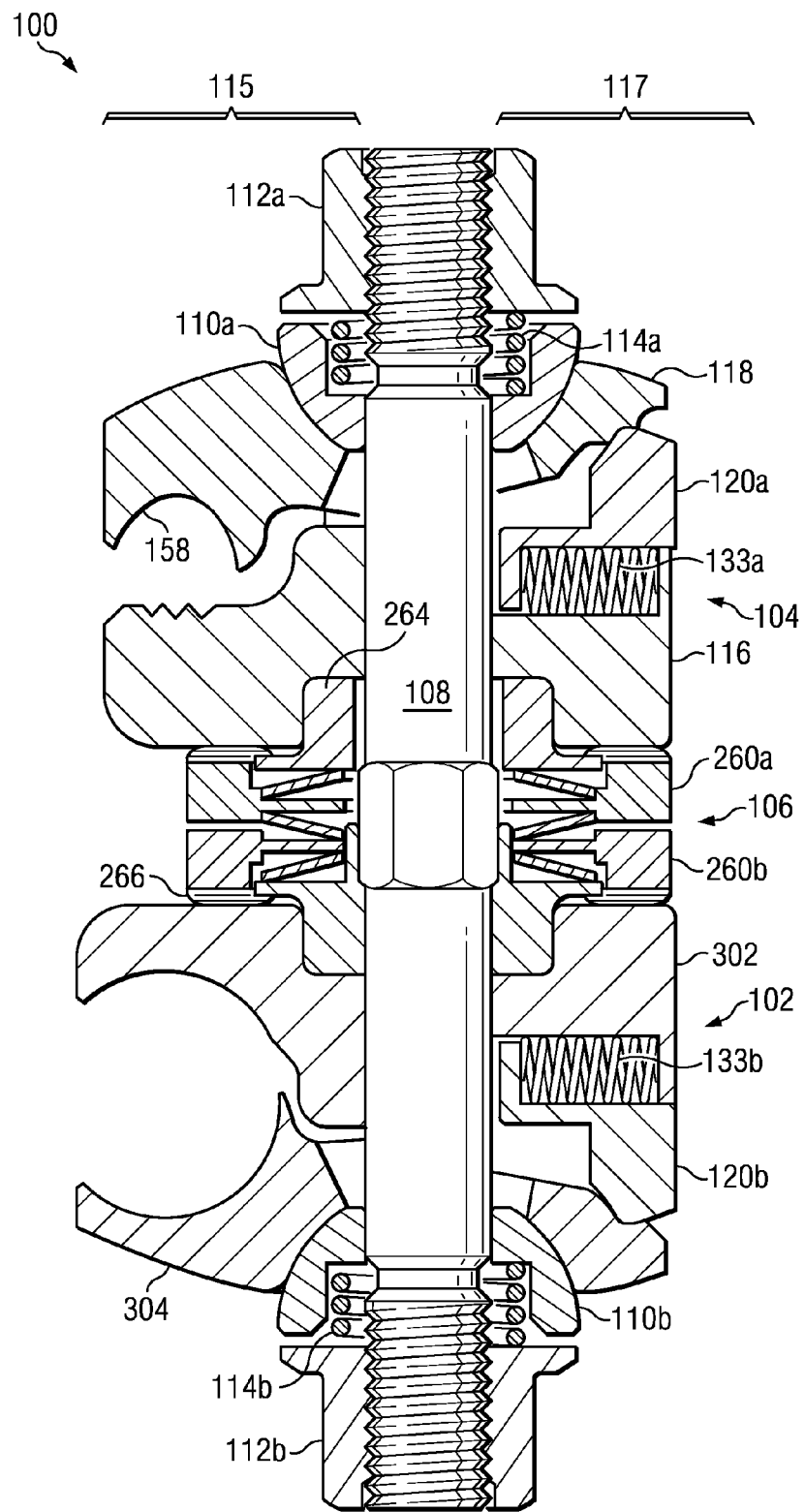
FIG. 4 is an illustration of a cross-sectional view of the clamping device of FIG. 2.
Figure 5:
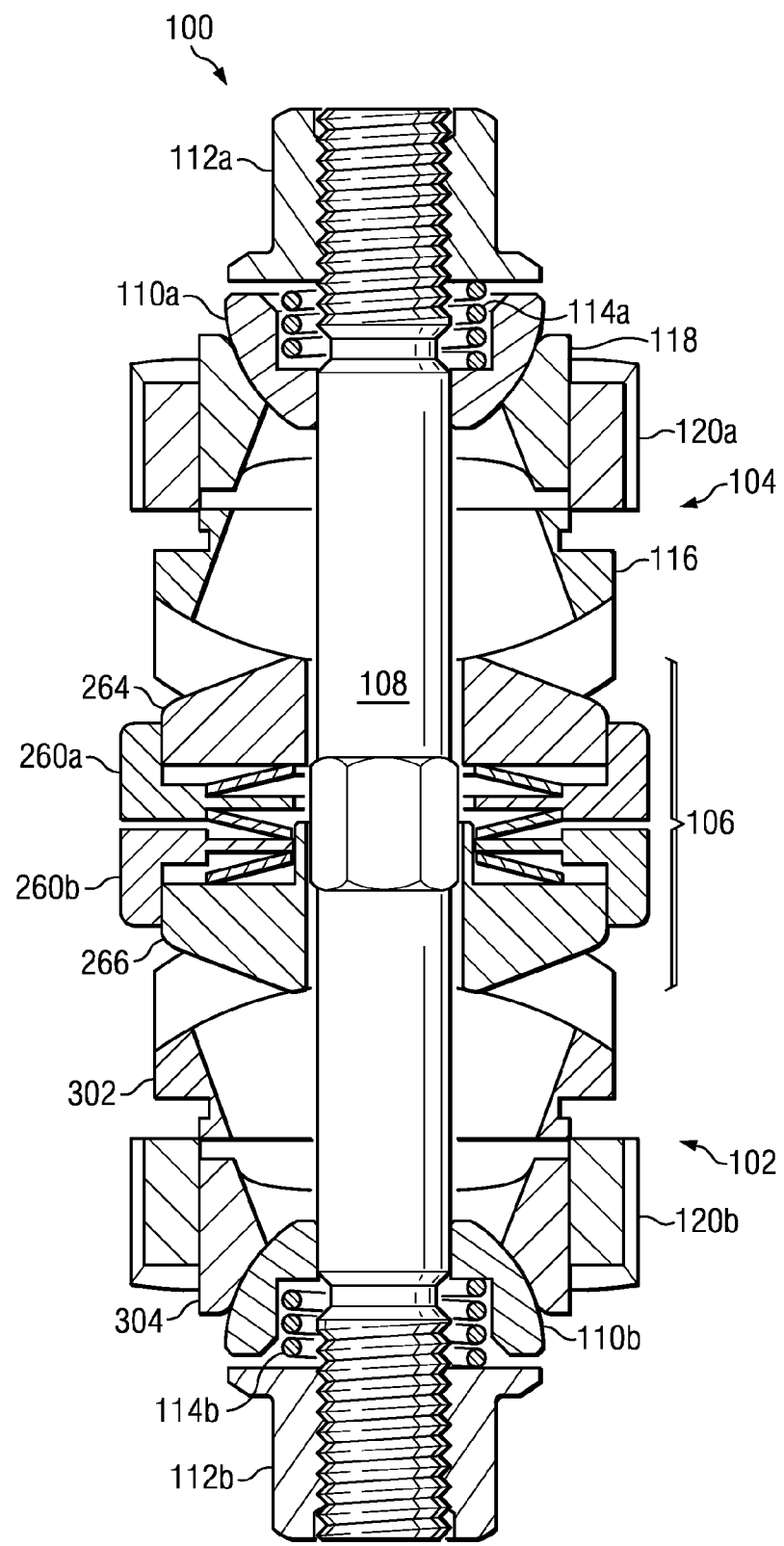
FIG. 5 is an illustration of a cross-sectional view of the clamping device of FIG. 2 taken transverse to the cross-sectional view in FIG. 4

FIGS. 2 and 3 respectively show an isometric view and a partially exploded view of the clamping device 100, while FIGS. 4 and 5 show cross-sectional views. Referring to FIGS. 2-5, in addition to the clamps 102, 104 and saddle assembly 106, the clamping device 100 includes a stud 108, spherical washers 110, and nuts 112. Biasing springs 114 are disposed about the stud 108 between the spherical washers 110 and the nuts 112. The stud 108 extends centrally through the device 100 and divides the device into a clamping side 115 representing the side of the device where fixation elements are held and introduced, and a rearward side 117 representing the side of the device opposite the clamping side.

Figure 6A:
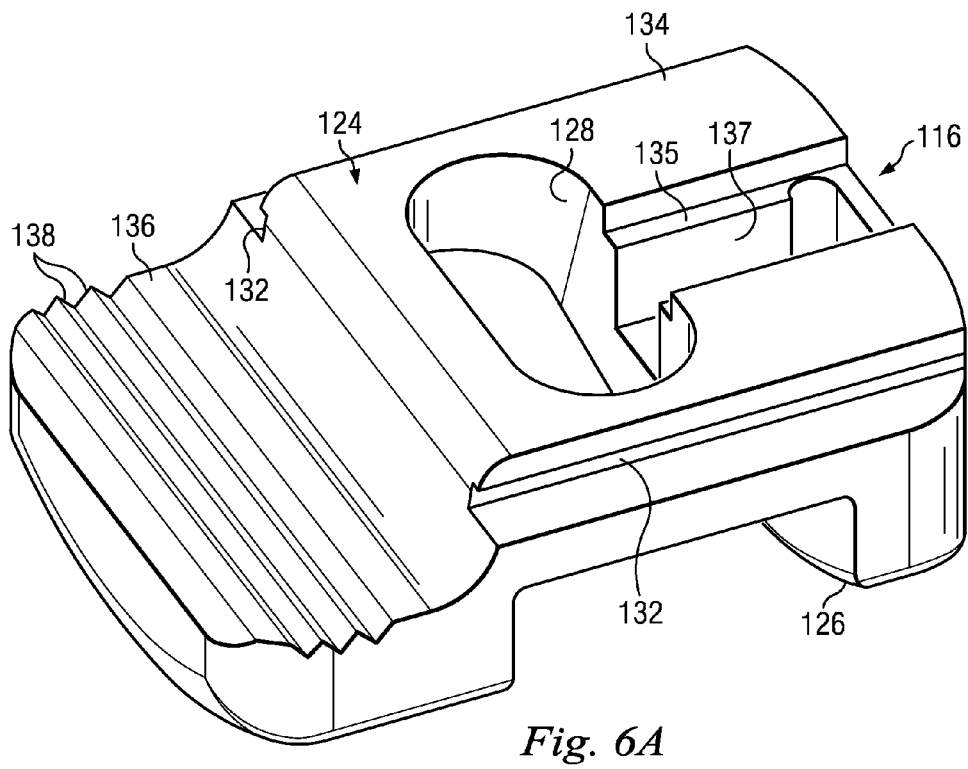
FIGS. 6A-6D are illustrations of an exemplary inner jaw of the clamping device in FIG. 2 in accordance with one exemplary aspect of the present disclosure.
Figure 6B:
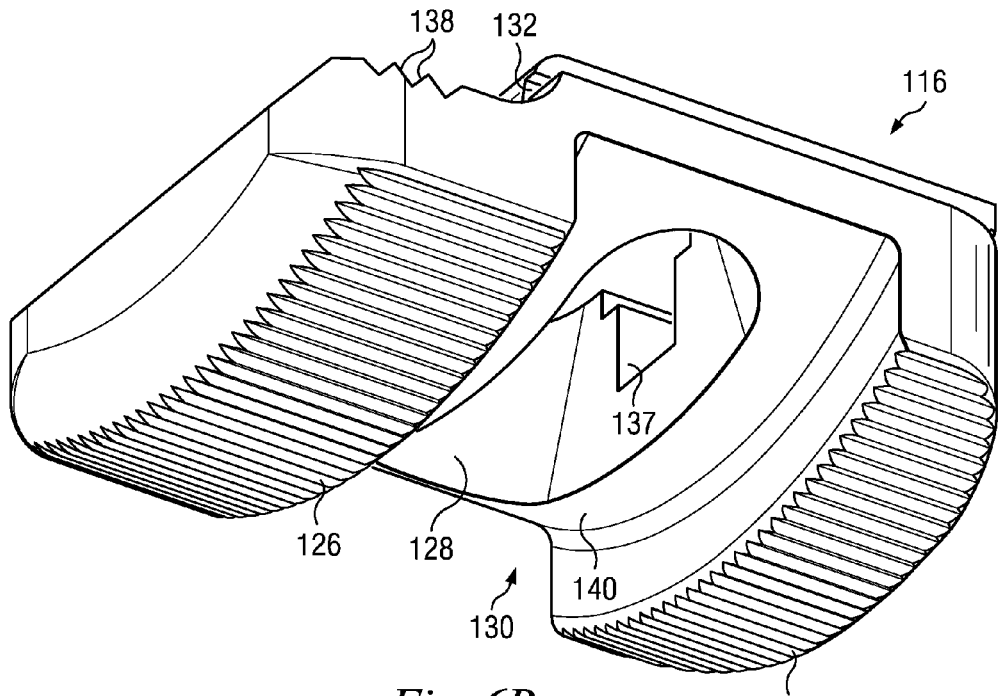
Figure 6C:
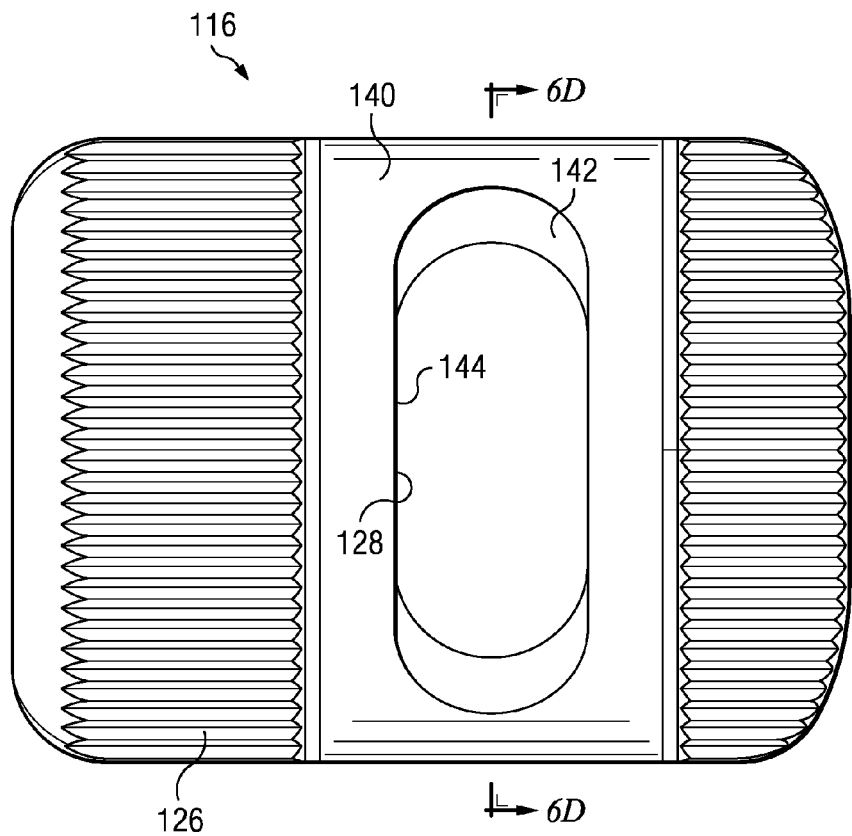

The clamps 102, 104 each include an inner jaw, an outer jaw, and a latch. The pin clamp 104 will be described first. The pin clamp 104 includes an inner jaw 116, an outer jaw 118, and a latch 120. The latch 120 operates to allow the clamps 102, 104 to open and operates to provisionally lock the clamps 102, 104 upon receipt of a fixation element. FIGS. 6A-6C show various views of the inner jaw 116. The inner jaw 116 cooperates with the outer jaw 118 to clamp onto and secure a pin, such as a bone pin. The inner jaw 116 includes an inner clamp face 124 that faces toward the outer jaw 118 and an outer clamp face 126 that interfaces with the saddle assembly 106. It also includes a central bore 128, a saddle assembly receiving area 130, and a latch race or guide 132.

The inner clamp face 124 includes a body surface portion 134 and a gripping surface portion 136. In the example shown, the body surface portion 134 and the gripping surface portion 136 are vertically offset. The body surface portion 134 is disposed generally toward the rearward side 117 (FIG. 4) of the clamping device 100 and the gripping surface portion 136 is disposed at the clamping side 115 (FIG. 4) of the clamping device 100. The body surface portion 134 includes an alignment groove 135 and a biasing channel 137 formed in the groove 135 that is sized and configured to maintain a biasing member (shown as biasing member 133 in FIGS. 3 and 4), such as a spring therein. The alignment groove 135 extends from the rearward side of the inner jaw 116 to the central bore 128. The biasing channel 137 in this example extends from the central bore 128 toward the rearward side of the inner jaw 116, but does not extend through the rearward side of the inner jaw 116. In some examples, the biasing channel 137 extends completely to the gripping surface portion 136 instead of ending at the central bore 128. Likewise, the alignment groove 135, in some examples, extends completely to the gripping surface portion 136. As will be explained below, the biasing channel 137 is shaped to receive the biasing member 133a, but also receives a downwardly extending tab on the latch 120 so that the biasing member 133 presses on the back of the biasing channel 137 and biases the latch 120 in the direction of the gripping surface portion 136 of the inner clamp face 124. The alignment groove 135 serves as a guide that permits passage of a corresponding element on the latch 120.

The gripping surface portion 136 is configured to interface with a fixation element such as a pin 14 from FIG. 1. In this example, the gripping surface portion 136 is substantially flat and includes a plurality of transverse teeth 138 formed therein. The plurality of transverse teeth 138 extend from one lateral side to the other and are configured to interface or engage with a fixation element that is held between the inner and outer jaws 116, 118. Other embodiments of the gripping surface portion 136 include a groove or a smooth surface.

Figure 6D:
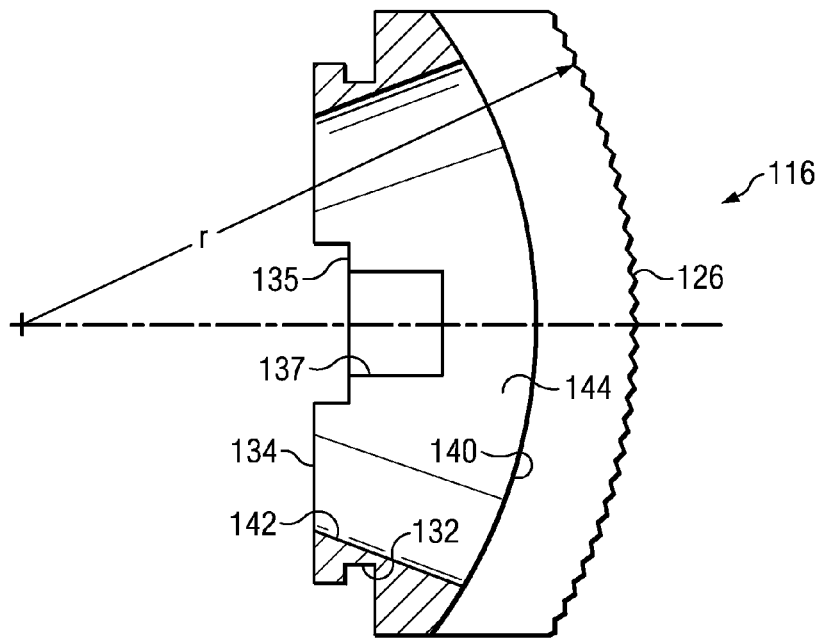

The outer clamp face 126 is a semi-cylindrical shaped surface that includes parallel, longitudinal splines shown in FIGS. 6B-6D. These are configured to interdigitate with the corresponding splines on the saddle assembly 106, as shown in FIGS. 2 and 3. The cylindrical shaped surface defines a radius r about which the inner jaw 116 pivots to provide the range of motion. Naturally, pivoting only occurs when the inner jaw 116 and the saddle assembly 106 are spaced so that the splines are not engaged. In some examples, in place of the splines, the inner jaw 116 includes knurling, a roughened surface or other friction inducing features are used to enable the inner jaw 116 and the saddle assembly to be selectively secured relative to each other.

The saddle receiving area 130 is a gap formed into the outer clamp face 126. It includes a recessed articulating surface 140 that is semi-cylindrical and concentric with the outer clamp face 126. The area 130 is shaped to receive a portion of the saddle assembly 106, and the articulating surface 140 engages and articulates with the saddle assembly 106. As such, unlike the outer clamp face 126, the articulating surface 140 is configured to provide smooth rotation about the axis.

The central bore 128 is a transversely extending opening having a generally rectangular shape with a width and a length and the length being longer than the width. In the embodiment shown, the central bore 128 has rounded or arching ends 142 separated by substantially parallel side edges spaced by the width. As best seen in FIG. 6C and the cross-section in FIG. 6D, the central bore 128 is cylindrical or conical-shaped at its ends 142 such that the bore length increases as the bore depth approaches the outer clamp face 126. In contrast, bore sidewalls 144 are substantially parallel to each other, maintaining the bore width substantially constant. The stud 108 fits within the central bore 128 as shown in FIG. 4, and provides only limited movement relative to the stud 108 in the longitudinal, or width direction. However, because the bore length is greater than the bore width, the inner jaw 116 may move relative to the stud 108 substantially more in the transverse, or length direction about the pitch axis 30, to change the pitch of the inner jaw 116 relative to the stud 108.

This ultimately changes the pitch of the inner jaw 116 relative to the saddle assembly 106. In the embodiment shown, the inner jaw 116 pivots relative to the saddle base 20 degrees in each direction, giving a pivot range of 40 degrees. However, it should be apparent that in other embodiments, the range of pivot articulation may be greater or less than 40 degrees, and may be affected by the diameter of the stud 108, the length of the central bore 128, as well as the angle of the bore ends 142.

The latch races 132 extend on lateral sides of the inner jaw 116. They act as sliding grooves that receive corresponding slide elements on the latch 120. The latch races 132 extend from the rearward side of the inner jaw 116 and they end above the gripping surface portion 136.

FIGS. 7A-7D show the outer jaw 118 in greater detail. The outer jaw 118 includes a front end 150, a rearward end 152, a central bore 160, an inner clamp face 154, and an outer clamp face 156. The inner clamp face 154 includes a pin-receiving transverse groove 158 adjacent the front end 150. The transverse groove 158 extends from one lateral side to another and is shaped to cooperate with the inner jaw 116 to receive and secure a bar, pin or other fixation element in place between the inner and outer jaws.

Figure 7A:
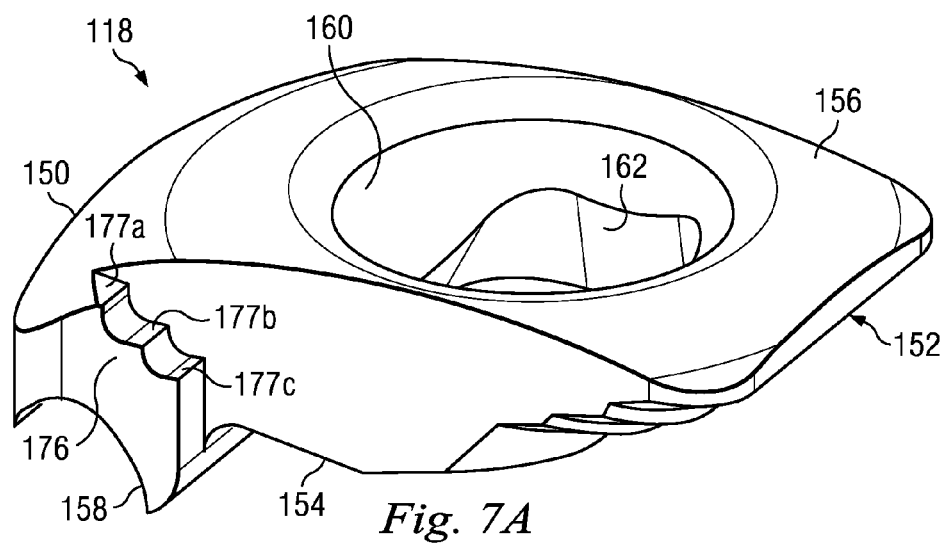
FIGS. 7A-7D are illustrations of an exemplary outer jaw of the clamping device in FIG. 2 in accordance with one exemplary aspect of the present disclosure.

As can be seen in FIG. 7A, a hook portion at the front end 150 defines a first portion of the transverse groove 158. As shown in the cross-section of FIG. 4, the groove 158 aligns with the teeth 138 on the inner jaw 116 to define a passage that captures a fixation element therein. The transverse groove 158 may be formed with a rounded bottom portion, flats, faces, or some combination of both.

Figure 7B:
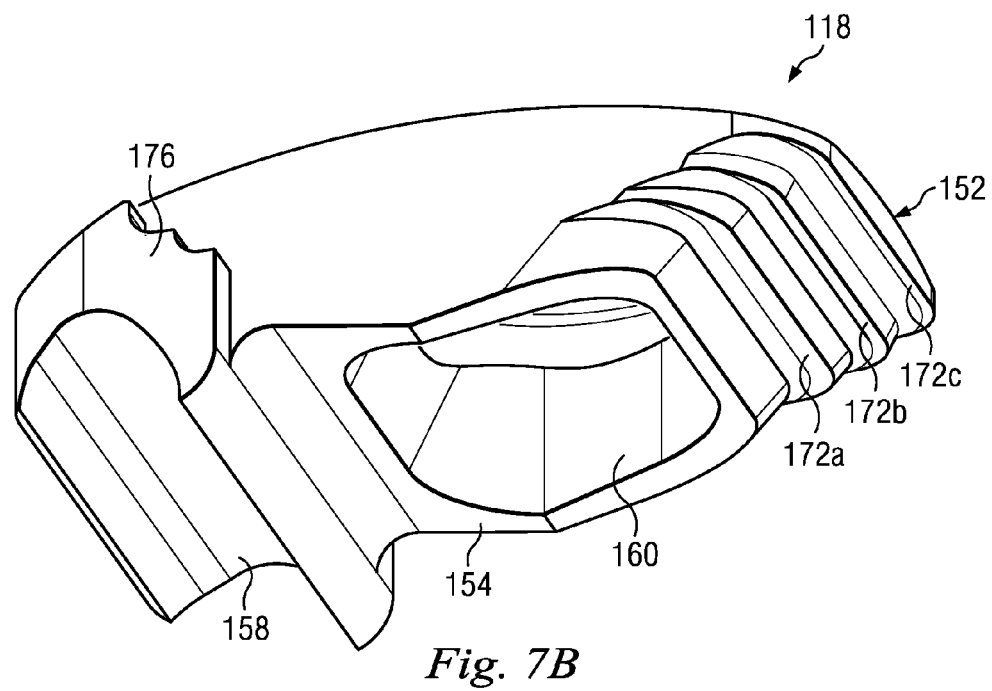
Figure 7C:
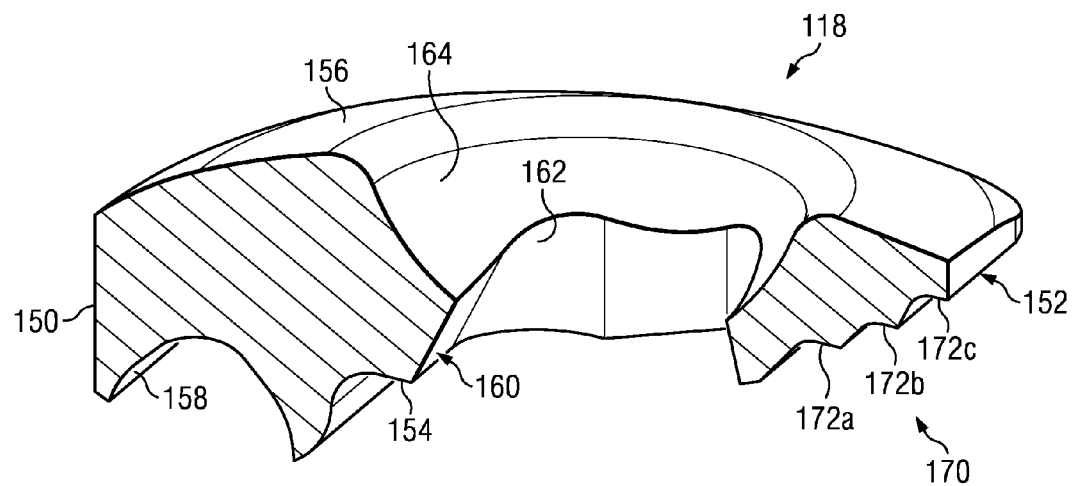
Figure 7D:
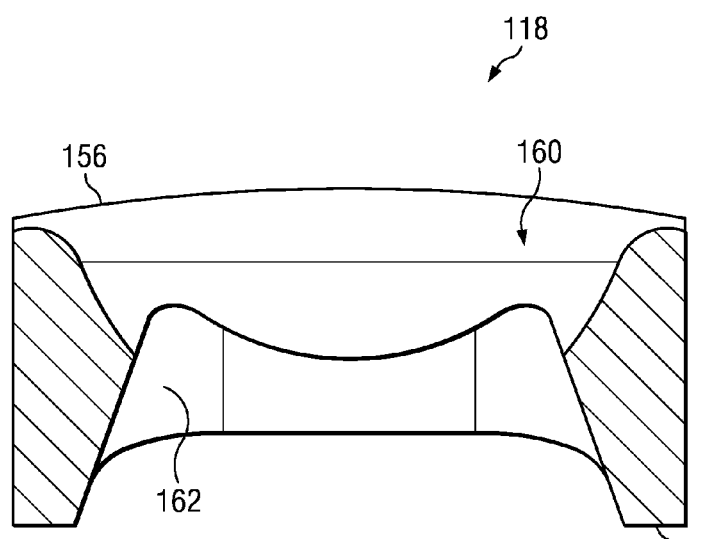

The central bore 160 includes features that enable it to provide articulation relative to the stud 108 in a manner that the outer jaw articulation matches that of the inner jaw 116. FIGS. 7C and 7D show the outer jaw 118 in cross-section and, along with the views in FIGS. 7A and 7B, provide an indication of the multiple surface aspects of the central bore 160. FIG. 7D is a section transverse to the section in FIG. 7C.

The central bore 160 is generally hour-glass shaped, with a narrowing neck 162 located between the inner clamp face 154 and the outer clamp face 156. At the inner clamp face 154, the central bore 160 is relatively rectangular shaped with a width and a length, the length being greater than the width. From the inner clamp face 154, the bore 160 tapers inwardly toward the neck 162, with the inner bore surfaces including curved portions as well as planar portions. As discussed further below, the central bore portion between the neck 162 and the inner clamp face 154 is arranged and shaped to permit articulation relative to the stud 108 in a manner to match articulation of the inner jaw 116 so that during articulation, the inner clamp face 154 of the outer jaw 118 faces the inner clamp face 124 of the inner jaw 116. Accordingly, in the embodiment shown, the central bore 160 is sized to permit pivot rotation in the lateral direction of the outer jaw 118 within, for example, a pivot range of 40 degrees, matching that of the inner jaw 116. As discussed above, other pivot ranges are contemplated and considered to be within the scope of this disclosure. Unlike the exemplary inner jaw 116, however, the outer jaw 118 in this embodiment is configured to also provide articulation in the longitudinal direction or front-to-rear direction. Accordingly as shown in FIG. 7C, the longitudinal direction also includes side walls tapering from the neck 162 toward the inner clamp face 154. As can be seen in FIG. 7C, these side walls are not symmetrically disposed, but permit more articulation in one longitudinal direction than the other. In the exemplary embodiment shown in FIG. 7C, for example, the sidewalls permit articulation from a center point in one direction of twenty degrees, and in the other direction, about 8 degrees. Accordingly, the outer jaw 118 is configured to pivot in the longitudinal direction relative to the stud 108 up to about 28 degrees. Of course other articulation ranges are contemplated and intended to fall within the scope of this disclosure.

The central bore portion between the neck 162 and the outer clamp face 156 is arranged and shaped to permit articulation relative to the stud 108 in a manner that permits the inner clamp face 154 to pivot and face the inner clamp face 124 of the inner jaw 116. Here, the central bore 160 widens from the neck 162 toward the outer clamp face 156. As can be seen in FIG. 7C, the central bore portion between the neck 162 and the outer clamp face 156 is nonsymmetrical. In addition, the inner walls are formed with concave curves 164 near the neck 162. These curves 164 are shaped to interface with the spherical washer 110 in FIG. 4 and provide an articulation surface for the outer jaw 118 to articulate relative to the spherical washer 110 as the outer jaw 118 displaces to open and close the clamp 104.

In use, the outer jaw 118 displaces relative to the stud 108 in the lateral direction as the inner jaw 116 pivots with respect to the saddle assembly 106. In addition, the outer jaw 118 displaces relative to the inner jaw 116 to open the jaws to receive a fixation element between the jaws and into the transverse groove 158. This displacement is in the longitudinal direction, and as shown in FIGS. 4 and 7C, the neck 162 of the central bore 160 is shaped large enough to permit pivoting about the center of the concave curves longitudinally as well as laterally.

Referring now to FIGS. 7A and 7B, the rearward end 152 of the outer jaw 118 includes a locking arrangement 170 shaped to contact or otherwise interface with the latch 120 to secure the outer jaw 118 in the open position, and shaped to release the outer jaw 118 so that it may pivot to capture a fixation element and secure it in the provisionally locked position. This locking arrangement 170 extends obliquely relative to the inner clamp face 154 and the outer clamp face 156 and includes a series of protruding engagement surfaces or catch surfaces 172a-c formed as steps or ridges that act as catches for the latch 120 when the clamp 104 is in the open position. Each catch surface 172a-c, in this embodiment, extends laterally across the rearward end 152 of the outer jaw 118. In this case, the outer jaw 118 includes three catch surfaces, each having a different elevation on the rearward end 152. These catch surfaces 172 are each located to come into play to capture a different sized fixation element. In the embodiment shown, the design is sized for 4 mm, 5 mm, and 6 mm fixation element. The role of the protruding catch surfaces 172 and their interaction with the latch 120 will become apparent in the discussion further below.

The outer jaw 118 also includes lateral shoulders 176 formed thereon. The lateral shoulders are shaped and configured to contact or otherwise interface with the latch 120 to limit jaw travel and mechanically interfere with opening of the pin clamp 104 when the latch 120 is in the closed position. The lateral shoulders 176 are disposed on both lateral sides of the outer jaw 118 and are formed adjacent the groove 158. In this embodiment, the lateral shoulders 176 include a series of engagement surfaces formed as steps or ridges that act as catch surfaces 177a-c for the latch 120 when the latch 120 is a closed position. In this example, the catch surfaces 177a-c include three levels, each increasing in elevation. As will become apparent from the discussion below, the catch surfaces 177a-c are formed to cooperate with the catch surfaces 172a-c to jointly cooperate with the latch 120 to secure the outer jaw 118 in a particularly closed position depending on the size of the fixation element being placed between the jaws. Accordingly, the clamp 104 can be secured in the provisionally locked position whether a small diameter fixation element or a larger diameter fixation element is being clamped in the clamp 104.

As will be come apparent from the discussion below, the lateral shoulders are disposed to cooperate with the latch 120 to mechanically prevent the front end of the jaws from separating. Because of this, the mechanical interference is located on the clamping side of the stud 108. In addition, as can be seen in the example shown the catch surfaces 177a-c are, at least in part, disposed at a location longitudinally in-line above the groove 158, where the fixation element is captured. Furthermore, as will become apparent from the discussion below, the latch 120 is configured to extend above a portion of the outer jaw 118 and extend below a portion of the inner jaw 116 as a locking latch that captures at least portions of the outer and inner jaws 116, 118 therebetween to prevent or limit separation of the clamping ends of the outer and inner jaws. In this way, the jaws can be mechanically prevented from separating and releasing the pin or rod.

Figure 8A:
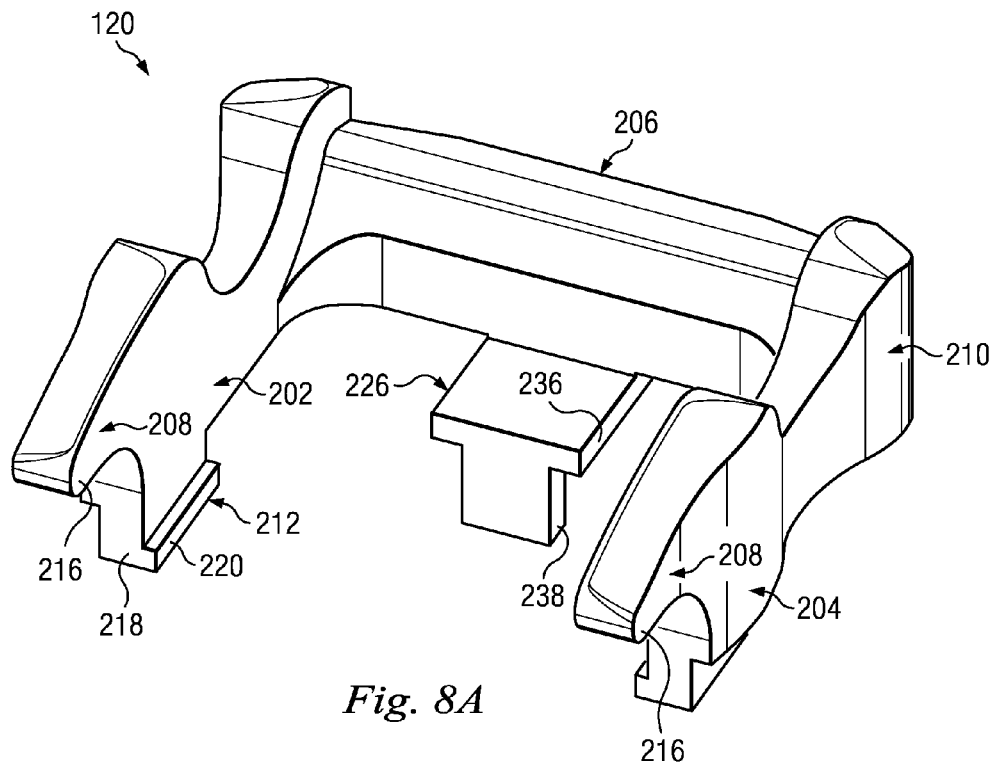
FIGS. 8A-8B are illustrations of an exemplary latch of the clamping device in FIG. 2 in accordance with one exemplary aspect of the present disclosure.
Figure 8B:
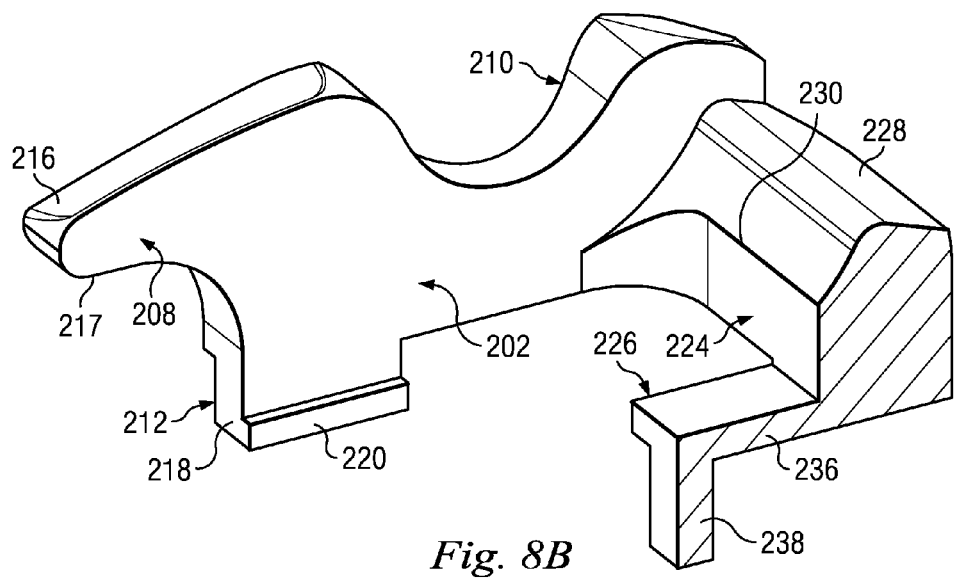

FIGS. 8A and 8B show the latch 120 in greater detail. The latch 120 is a U-shaped element arranged to interface with both the inner and outer jaws 116, 118 to lock the jaws in a provisionally locked position. The latch 120 includes first and second lateral aims 202, 204 connected by a rearwardly disposed cross bar 206.

The first and second lateral arms 202, 204 each include a forward portion 208, a rearward portion 210, and a hook portion 212. The forward portion 208 includes a forwardly projecting leading tip 216 that is located to interface with the lateral shoulders 176 of the outer jaw 118 when the latch 120 is in a locking position. In this example, the leading tip 216 is disposed at a location on the latch 120 to extend above at least a portion of the outer jaw 118. The leading tip 216 is relatively narrow, and it extends from the main body of the latch at a location an in a manner that it can extend above the rod or pin carried in the clamp assembly 104. In the example shown the leading tip 216 includes an engagement surface 217 configured to engage the outer jaw 118. In other embodiments however the projection leading tip 216 is configured to engage the fixation element itself, securing it against the inner jaw 116 and preventing removal. An edge of the latch 120 extends in a curve from the leading tip 216, extending in a substantially transverse direction, to the latch body, in a substantially longitudinal direction.

The rearward portion 210 is formed, at least in the embodiment shown, with an ergonomic finger grip to permit simple grasping by the user. As will become apparent in the discussion below, a user will grasp the latch 120 by pinching on the lateral arms, for example, between a thumb and forefinger, and displacing the latch 120 rearwardly to open the clamp 104. In this example, the rearward portion 210 connects with the crossbar 206.

The hook portion 212 projects from a bottom of the latch 120. The hook portion 212 is shown as being substantially disposed toward the forward portion 208. However, in other embodiments, the hook portion 212 extends along the entire bottom portion of the latch 120 to the rearwardly disposed cross-bar 206. The hook portion 212 includes a base 218 and a projection 220, with the projection extending laterally inward. The hook portion 212 is located and configured to be received in and slide relative to the latch race 132 in the inner jaw 116. Accordingly, it limits the sliding motion of the latch 120 to a forward and rearward direction only.

The rearwardly disposed cross bar 206 extends between and connects the rearward portions 210 of the first and second lateral arms 202, 204. It is a rigid structure that includes a main body portion 224 and a biasing tab 226.

The main body portion 224, best seen in the cross-sectional view of FIG. 5B, includes a lock close interface 228 and a lock open interface 230. The lock-close interface 228 is shaped and configured to interface with the catch surfaces 172 on the outer jaw 118 to place the outer jaw 110 in the provisionally locked condition. As will become apparent further below, the lock-close interface 228 interfaces with the outer jaw 118 and mechanically separates the rearward ends of the inner and outer jaws 116, 118. In this example, the crossbar 106 itself acts as a wedge that is selectively disposed between the inner and outer jaws 116, 118 to limit the relative rotation of the jaws, thereby cooperatively limiting the separation distance of the jaws at the clamping side. Accordingly, the lock-close interface 228 is the surface that interfaces with the outer jaw 118 to prevent the outer jaw 118 from moving relative to the inner jaw 116 and opening the jaws. The lock open interface 230 is a surface on the main body portion 224 that engages the outer jaw 118 when the jaw is in an open condition. That is, with the latch 120 disposed rearwardly so that the cross-bar 206 is not interfering with rotation of the outer jaw 118, the lock open interface 230 rests against a rearward surface of the outer jaw 118. As such, the lock open interface 230 may cooperate with the rearward end 152 of the outer jaw 118 to permit the outer jaw 118 to rest in the opened receiving position.

The biasing tab 226 projects downwardly and is configured to cooperatively engage the inner jaw 116. It is centrally disposed on the crossbar 206, and it comprises an alignment portion 236 and a load tab 238. The alignment portion is a transversely extending portion shaped and arranged to fit within the alignment groove 135 in the inner jaw 116. As such, it has a width that permits smooth translational movement within the alignment groove 135, while providing structural support. It is disposed below the main body portion 224 so that as the cross bar 206 translates along the body surface portion 134 of the inner clamp face 124, the alignment portion 236 travels within the alignment groove 135. It has a first end that extends from the main body portion 224 toward the clamping end of the clamp 100 and it has a second end that ends substantially flush with a rearward surface of the crossbar 206.

The load tab 238 extends at a right angle from the alignment portion 236 and is configured to extend into the biasing channel 137 in the alignment groove 135. As such, it has a width less than the width of the alignment portion 236. The load tab 238 has a biasing surface thereon that interfaces with a biasing element 133 shown in the cross-sectional view of FIG. 4.

The interaction of the different components of the pin clamp 104 will now be described with reference to FIGS. 9-16. FIGS. 9, 11, 13, and 15 show cross-sectional views showing the interaction between the catch surfaces at the rearward end of the pin clamp 104. FIGS. 10, 12, 14, and 16 show the interaction between the catch surfaces at the forward or clamping side of the pin clamp 104.

Figure 9A:
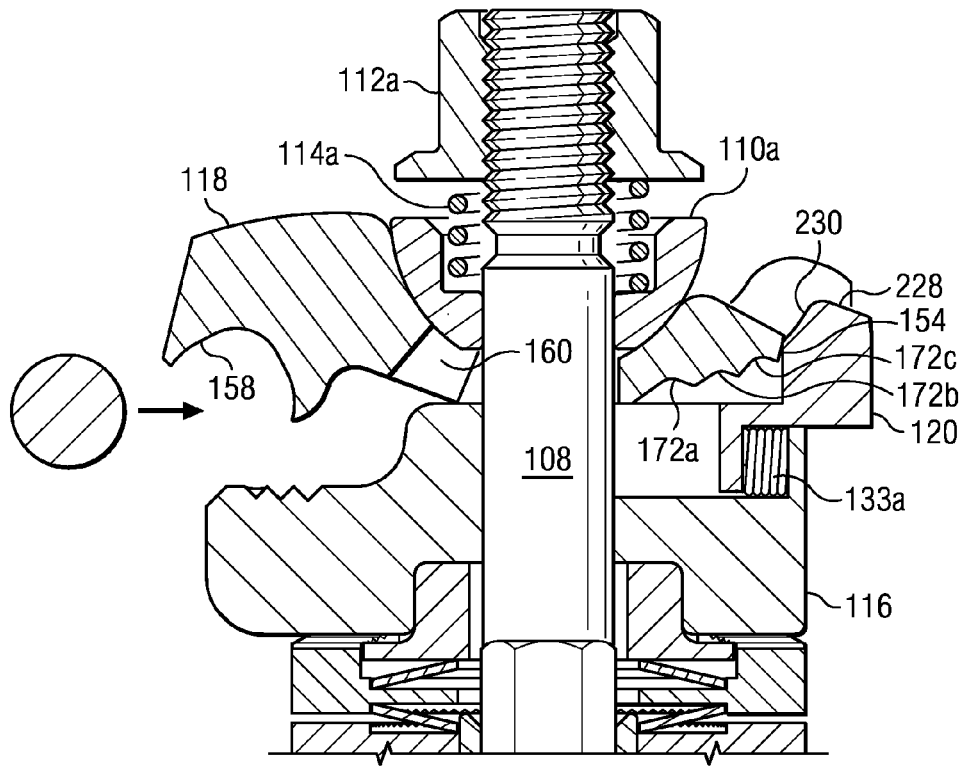
FIG. 9A is an illustration of a cross-sectional view of a clamp of FIG. 2 in an open condition.
Figure 9B:
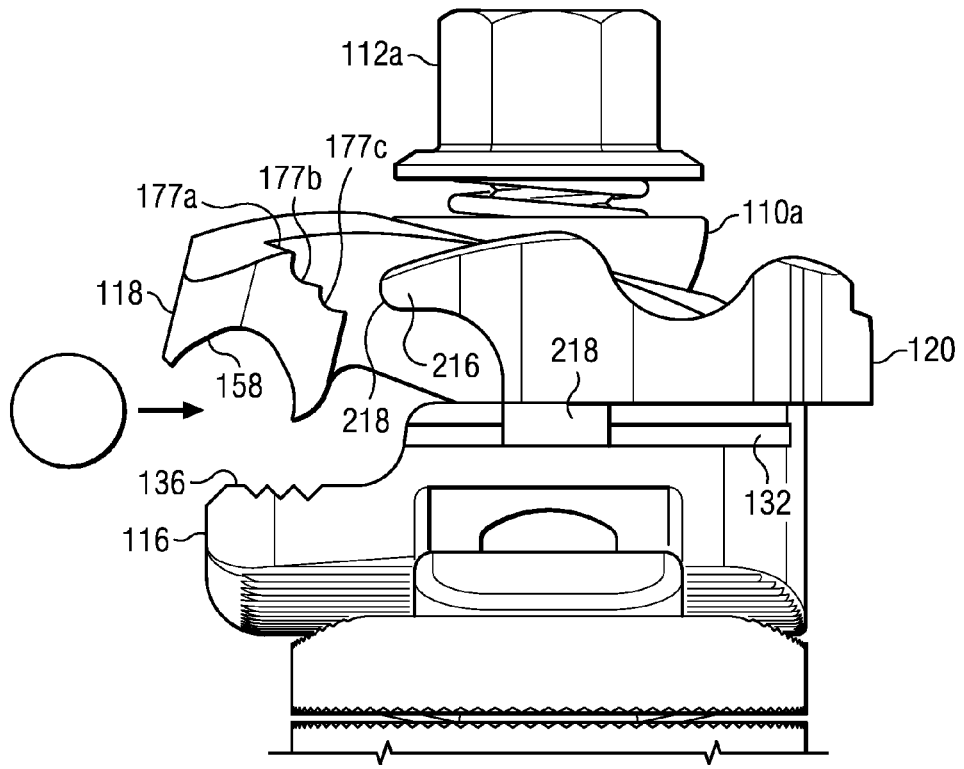
FIG. 9B is an illustration of a plan view of the clamp of 9A in an open condition.

FIGS. 9A and 9B show the pin clamp 104 in an open, bar-receiving condition. FIGS. 10A and 10B show the clamp 104 after having received a relatively large fixation element, such as a 6 mm pin, FIGS. 11A and 11B show the clamp 104 holding a relatively medium sized fixation element, such as a 5 mm pin, and FIGS. 12A and 12B show the clamp 104 holding a relatively small fixation element, such as 4 mm pin.

Referring first to FIG. 9A, the clamp 104 is arranged in an open, bar receiving condition. To be in this position, the latch 120 may be pulled rearwardly. This action compresses the biasing element 133 between the load tab 238 and the rear wall of the biasing channel 137. As the latch 120 is pulled rearwardly, the cross bar 206 moves rearwardly, out from between the inner and outer jaws 116, 118. As the restraints on the outer jaw movement are displaced, the biasing spring 114 presses downwardly on the outer jaw 118, causing the outer jaw 118 to rotate about the spherical nut 110 and open to the bar receiving position. At the same time that the crossbar 206 moves rearwardly out from between the inner and outer jaws 116, 118, the leading tip 216 of the latch 120 moves rearwardly out from above the catch surfaces 177 on the lateral shoulders 176 of the outer jaw 118 to the position shown in FIG. 9B.

With the latch 120 in the condition shown in FIGS. 9A and 9B, the pin clamp 104 is ready to receive a fixation element therein. The fixation element is introduced laterally into the jaws. It is placed through the opening of the jaws and into the passage defined between the jaws. Depending on the size of the fixation element and the size and arrangement of the jaws, the fixation element may not be fully disposed between the jaws when it is in the passage, but may have some surface portion outside of the jaws. With the fixation element in the passage, further advancement presses against the rearward side of the transverse groove 158. This causes the outer jaw 118 to displace about the spherical washer 110. As the outer jaw 118 rotates, its rearward end 152 rises above the lock open interface 230, allowing the latch 120 to advance to a position between the inner and outer jaws 116, 118. As it advances, the biasing element moves the latch 120 toward the fixation element so that the lock close interface 228 engages with the first catch surface 172, thereby preventing rotational motion in the reverse direction. With the outer jaw 118 fully rotated, the latch 120 may be advanced under spring force to a position between the inner and outer jaws 116, 118, providing a mechanical barrier against opening. In this condition, the fixation element is provisionally locked within the clamp. This is illustrated in FIG. 10A, with a 6 mm fixation element.

At the same time that the latch 120 advances to engage the first catch surface 172, the leading tip 216 of the latch 120 moves forwardly toward the clamp end to a position above the first catch surface 177 of the lateral shoulders 176 of the outer jaw 118. Thus, the leading tip 116 moves into a position that prevents premature separation of the jaws. This is shown in FIG. 10B.

With the fixation element provisionally locked in the clamp 104, the clamp can be moved axially along the fixation element and may be rotated about the fixation element. This allows the health care provider to manipulate the fixation frame to a desired orientation. If the clamp 104 is to be removed, the latch 120 is manually pulled back to allow the jaws to open so the rod can exit the channel. The fixation clamp system can be locked by tightening the nuts 112, which tighten down the whole system, including the biasing springs 114a, the jaws, and the saddle assembly 106.

If a smaller fixation element is being introduced into the pin clamp 104 than the one shown in FIGS. 10A and 10B, then the fixation element may continue to advance further into the space between the inner and outer jaws 116, 118. Accordingly, the outer jaw 118 may continue to rotate about the spherical washer 110 until the second catch surface 172 clears the crossbar 206, and the lock close interface 228 engages with the second catch surface 172b, thereby preventing rotational motion in the reverse direction. This additional rotation of the outer jaw 118 results in the transverse groove 158 moving closer to the inner jaw 116, thereby further reducing the size of the passage containing the fixation element. This is shown in FIG. 11A. FIG. 11B shows the leading tip 216 of the latch 120 moved forward to a position above the second catch surface 177b of the lateral shoulders 176 of the outer jaw 118. Thus, the leading tip 216 moves into a position that prevents premature separation of the jaws. FIGS. 12A and 12B each show the pin clamp 104 with a 4 mm fixation element. In FIG. 12A, the lock close interface 228 engages the third catch surface 172, thereby preventing rotational motion in the reverse direction. FIG. 12B shows the leading tip 216 of the latch 120 moved forward to a position above the third catch surface 177a of the lateral shoulders 176 of the outer jaw 118.

The catch surfaces 172, 177 are designed so that they just clear the crossbar 206 or are disposed to be just cleared by the latch 120 when certain sized rods have been placed as far as they can go into the passage between the inner and outer jaws 116, 118. That is, the spacing and depth of cut of the catch surfaces 172, 177 are selected so that when a 6 mm fixation element is introduced into the passageway and advanced until the fixation element is disposed at a location substantially against both the inner and outer jaws, the first catch surface 172 clears the crossbar 206 and cooperates with the lock open interface 228 to prevent removal, while the first catch surface 177 cooperates with the leading tip 216 of the latch 120 to prevent removal. Accordingly, the size of the fixation element may be a factor that limits how far it may be forced into the passage.

The example shown herein discloses a locking mechanism that includes the simultaneous action of both a rearward locking element and front locking element, with the rearward locking element being formed by latch crossbar 206 acting as a structural wedge or stop that enters between the inner and outer jaws 116, 118, and the front locking element being formed with the leading tip 216 above the catch surfaces 177 of the lateral shoulders 176. However, other embodiments include just one locking element or the other. For example, one example of a device according to the present disclosure employs only the front locking element where the leading tip 216 of the latch 120 cooperates with the catch surfaces 177 on the lateral shoulders 176 of the outer jaw 118 to prevent the jaws from opening and prematurely releasing the fixation element held therein. As such, in this embodiment, the latch 120 is designed to not limit the rotation of the jaws on the rearward side of the pin clamp 104. Likewise, in other embodiments, a device according to the present disclosure employs only the rearward locking element where crossbar 206 engages the rearward side of the jaws 216, 217 to prevent the jaws from opening and prematurely releasing the fixation element held therein.

Having described the pin clamp 104 and its operation, the following disclosure relates to the rod clamp 102. Much of the discussion above relating to the pin clamp 104 is equally applicable to the rod clamp 102 and to avoid duplicity will not all be repeated. Nonetheless, it should be apparent that the pin and rod clamps share many common features that operate in similar manners. Here, the rod clamp 102 is shown with single catch surfaces rather than the pluralities of stepped catch surfaces discussed above. This is done to show another possible variation among the contemplated clamps. It should be understood that rod clamps configured similar to the pin clamps and intended to hold more than one size bar, are envisioned and fall within the scope of this disclosure. Likewise, pin clamps having only single catch surfaces are also envisioned.

FIGS. 3-5 show the rod clamp 102 as having and an inner jaw 302 and an outer jaw 304. The inner jaw 302 is shown in detail in FIG. 13. As can be seen, the inner jaw 302 differs from the inner jaw 116 in the size and shape of the gripping portion of the jaw. Here, the inner jaw 302 includes an inner clamp face 306 that faces toward the outer jaw 304 and an outer clamp face 308 that interfaces with the saddle assembly 106.

The inner clamp face 306 includes a gripping portion as a transverse groove 310 for receiving a fixation element, and a body surface portion 312. The transverse groove 310 is located at a clamping end 314 of the inner jaw 302.

Figure 13A:
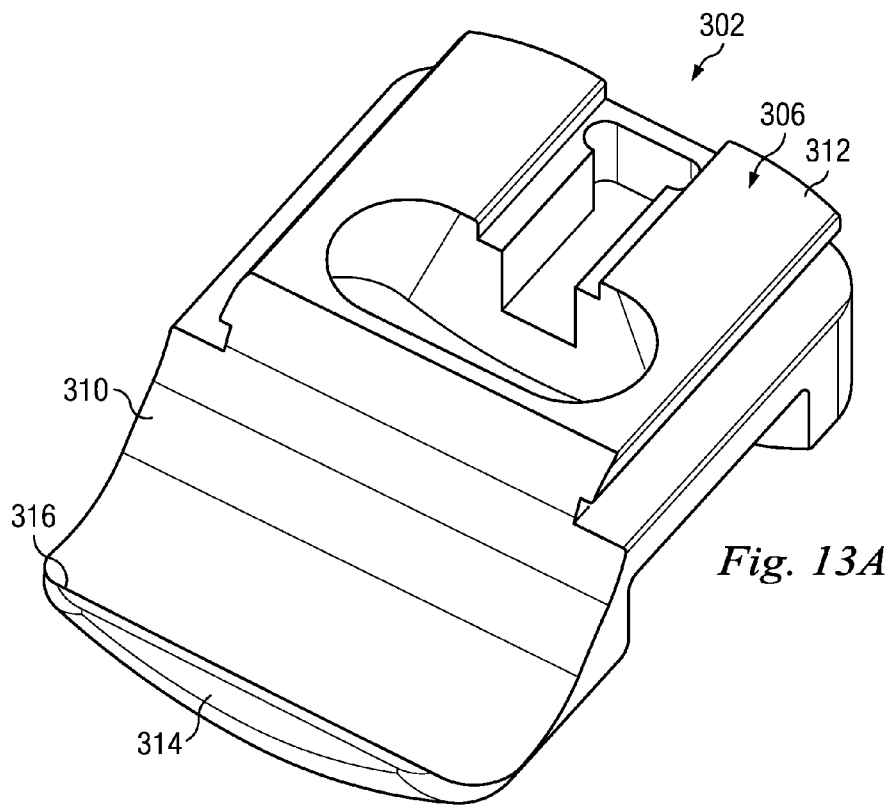
FIGS. 13A-13B are illustrations of an exemplary inner jaw of another clamp of the clamping device in FIG. 2 in accordance with one exemplary aspect of the present disclosure.
Figure 13B:
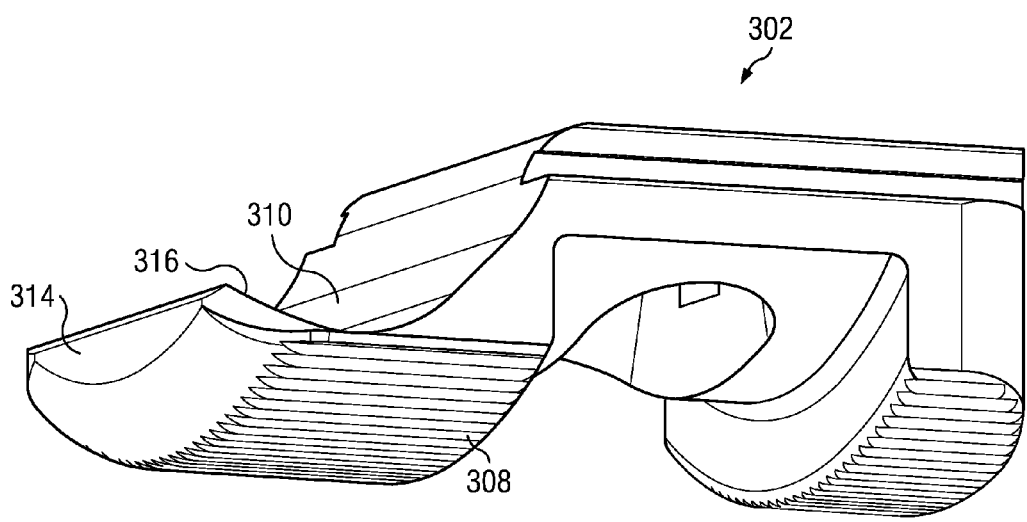

As shown in FIG. 13A, the transverse groove 310 extends from one lateral side to another and is shaped to receive a bar, pin, or other fixation element. The transverse groove 310 is formed between a hook portion 316 at the front end of the inner jaw 302 that secures a fixation element in the clamp. The transverse groove 310 may be formed with a rounded bottom portion or may be formed of a series of flats or faces. Some embodiments may have a combination of both curves and faces. The depth of the transverse groove 310 may vary between different clamps or jaws depending on the size of the fixation element intended to be gripped by the clamp. In some embodiments, because the cross-section of the fixation element may have shapes other than circular, the groove 310 may be shaped to also matingly interface with these bars and pins. For example, the groove 310 may include teeth, cut-outs, or other features that interface with bars having a non-smooth or non-circular outer surface. In some examples, the groove 310 includes two laterally extending teeth intended to increase the frictional gripping on the fixation element carried in the clamp.

Figure 14A:
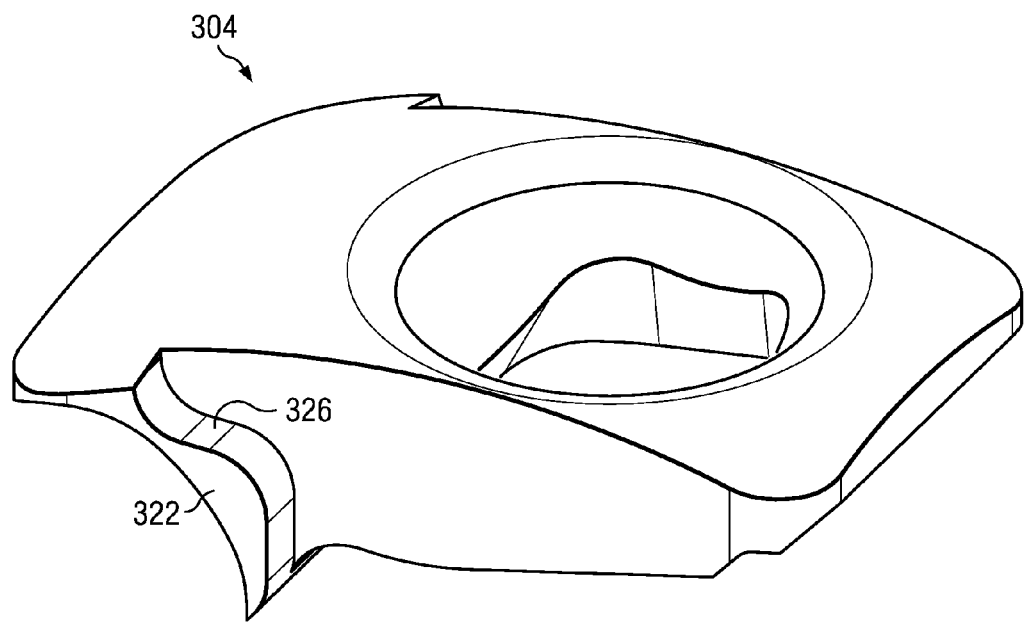
FIGS. 14A-14B are illustrations of an exemplary outer jaw of the other clamp of the clamping device in FIG. 2 in accordance with one exemplary aspect of the present disclosure.
Figure 14B:
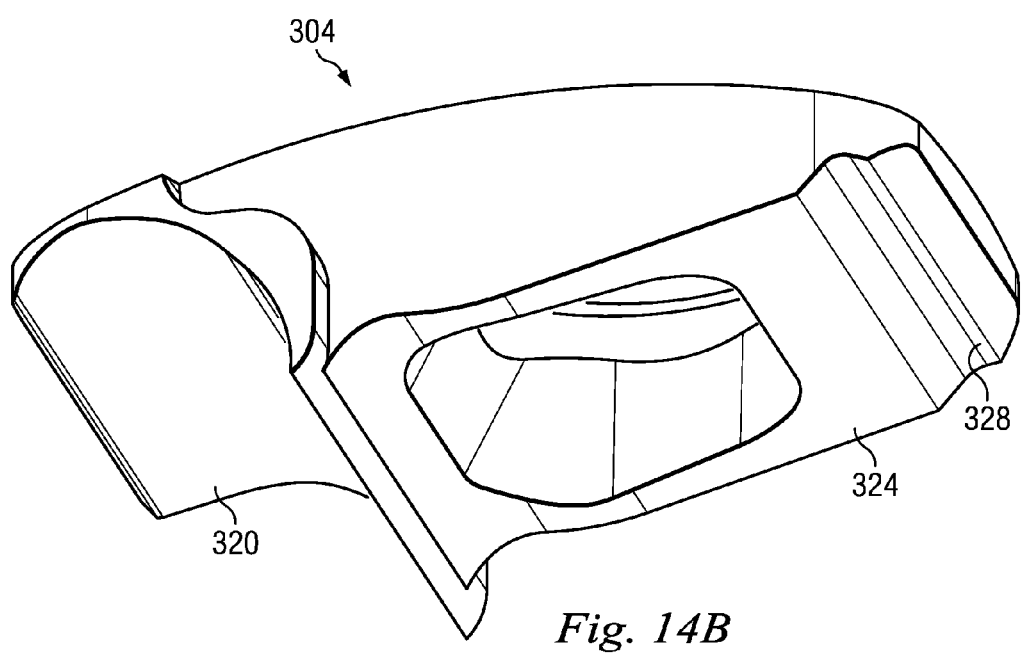

FIGS. 14A-14B show the outer jaw 304 in greater detail. Again, the outer jaw 304 is configured and arranged in many ways to be the same as the outer jaw 118 discussed above and that description is relevant here. Some of the differences are described below.

First, the outer jaw 304 includes a groove 320 having a shape different than the shape of the groove described with reference to the outer jaw 118 of the pin clamp 104. However, the groove 320 is much like the groove 310 discussed above with respect to the inner jaw 302, and that description is relevant and applies to the groove 320. Second, this example includes only a single step or catch surface, rather than three steps or catch surfaces, for locking the inner and outer jaws together to prevent the jaws from opening and prematurely releasing the fixation element held therein. That is, the outer jaw 304 includes lateral shoulders 322 and an inner clamp face 324.

The outer jaw 304 includes a locking mechanism formed of two locking arrangements shaped to contact or otherwise interface with the latch 120 to secure the outer jaw 304 in the open position, and shaped to release the outer jaw 304 so that it may pivot to capture a fixation element and secure it in the provisionally locked position. These are described as the catch surfaces. The lateral shoulders 322 in this example include a single catch surface 326. The catch surface 326 is configured to cooperate with the latch 120 to secure the clamp device in closed position on the clamping side of the clamping device 100. Like the catch surfaces 177 discussed in the embodiments above, the catch surface 326 is disposed at least partially above the passage formed by the groove 320. As such, the end of the latch may project over a portion of a fixation element disposed in the groove. In some examples, the latch may engage the fixation element itself in place of the catch surfaces on the outer jaw 304.

The inner clamp face 324 includes a single engagement surface or catch surface 328 formed as a step or ridge that acts as a catch for the latch 120 when the clamp 102 is in the open position. The catch surfaces 328 is located to come into play to capture a particularly sized fixation element.

The rod clamp 102 with its inner and outer jaws 302, 304, like the pin clamp 104 discussed above, is arranged to interface with a latch 120b described above and operating in the same manner discussed above. However, instead of being arranged to lock on different catch surfaces based on rod size, the rod clamp is configured to have only a single open or closed condition. Even still, it operates in the same manner with the cross bar 206 of the latch 120 being disposed between the inner and outer jaws 302, 304 when the clamp 102 is in a locked condition. Likewise, the leading tip 216 of the latch 120 moves to engage or disengage the catch surface 326 on the lateral shoulders 322 of the outer jaw 118 to mechanically permit or prevent separation of the front of the inner jaw 302 from the outer jaw 304.

Figure 15A:
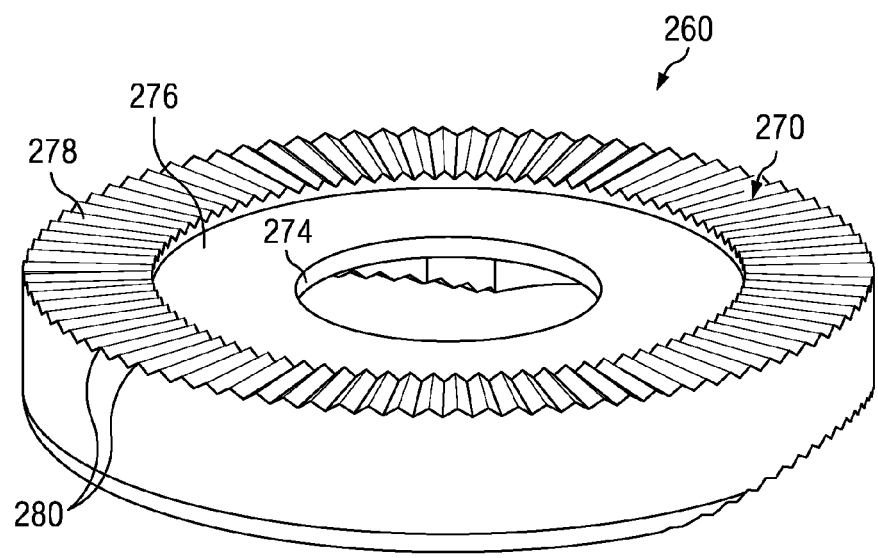
FIGS. 15A-15B are illustrations of an exemplary saddle of the clamping device in FIG. 2 in accordance with one exemplary aspect of the present disclosure.
Figure 15B:
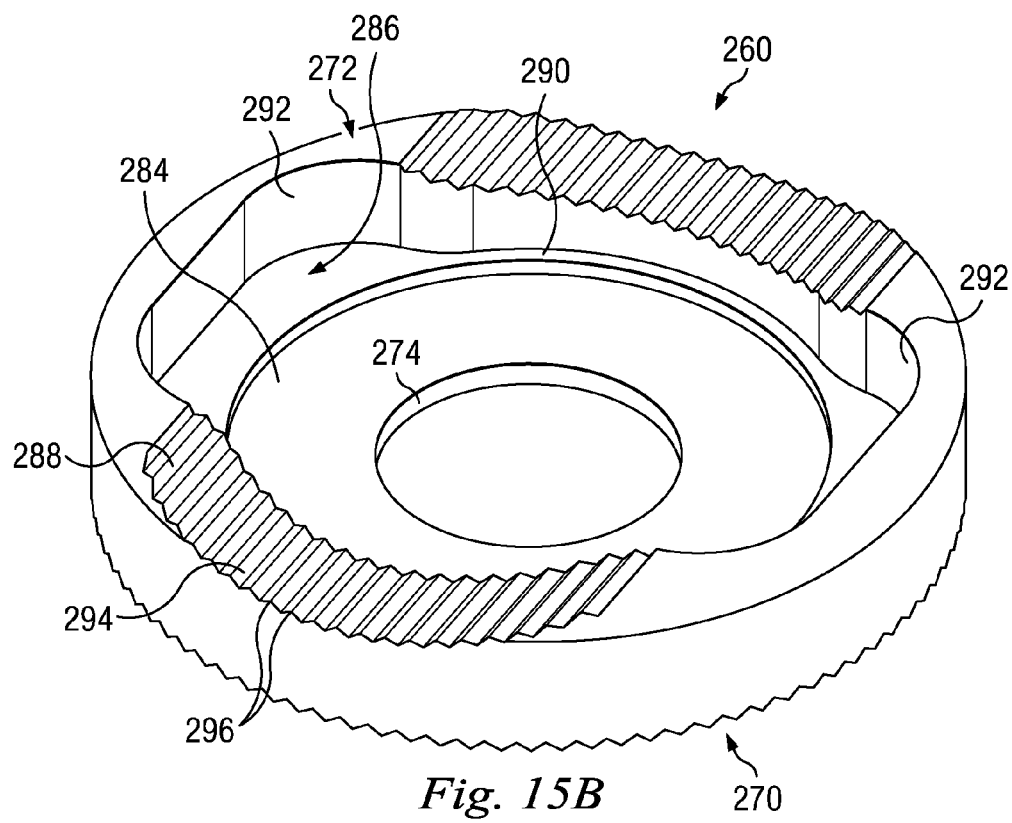
Figure 16:
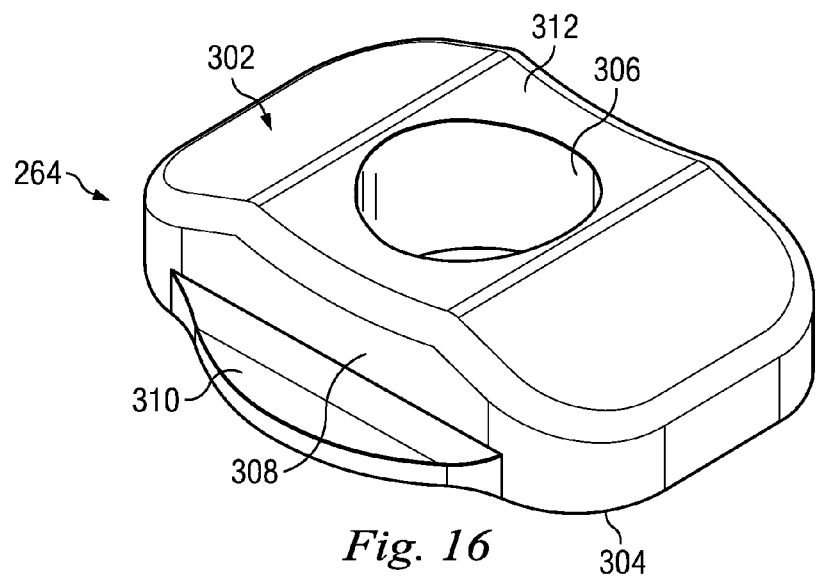
FIG. 16 is an illustration of an exemplary spacer of the clamping device in FIG. 2 in accordance with one exemplary aspect of the present disclosure.
Figure 17A:
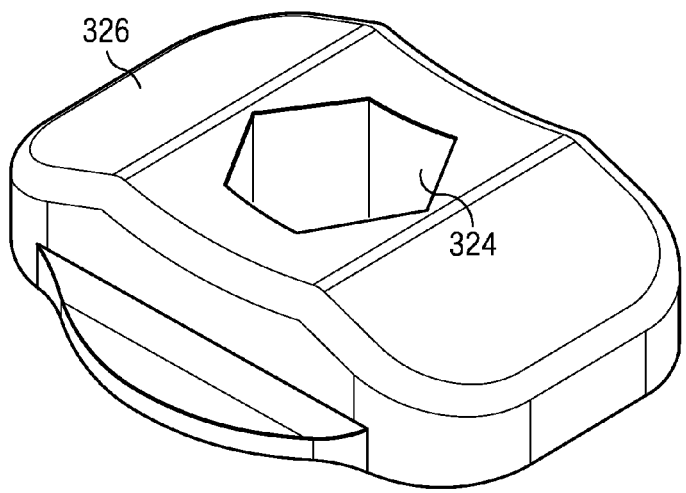
FIGS. 17A-17B are illustrations of an exemplary spacer of the external fixation system in FIG. 1 in accordance with one exemplary aspect of the present disclosure.
Figure 17B:
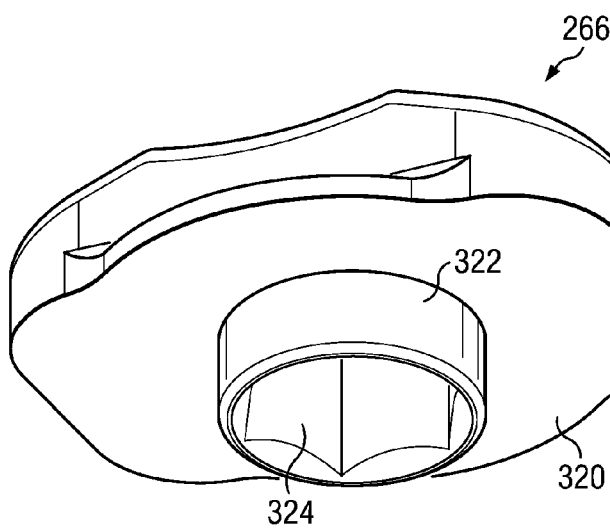

FIGS. 15-17 show components of the exemplary saddle assembly 106. The saddle assembly 106 is arranged to permit the bar clamp 102 to rotate relative to the pin clamp 104 when the clamping device 100 is in an unlocked or in a provisionally locked condition. In addition, the saddle assembly 106 provides a foundation or base for each of the bar clamp 102 and the pin clamp 104 to each independently pivot about the pitch axis 130 in FIG. 2. FIG. 4 shows a cross-section of the saddle assembly 106 disposed about the stud 108. The saddle assembly 106 includes a first saddle 260a, a second saddle 260b, a thru spacer 264, and a hex spacer 266. Biasing elements, such as spring washers 268a-c, separate each of the saddles 206a, 206b and the spacers 264, 266. FIGS. 15 and 15B show an exemplary saddle 260, FIG. 16 shows the exemplary thru spacer 264, and FIGS. 17A-17B show the exemplary hex spacer 266. The first and second saddles 260a, 260b are, in this embodiment, identical to each other and are both represented by the exemplary saddle 260 in FIGS. 15A-15B.

Referring to these figures, the saddle 260 includes an inner facing side 270 and an outer facing side 272. FIGS. 3 and 4 show the inner facing side of the saddle 260a facing the opposing second saddle 260b, while the outer facing side 272 is arranged to face the adjacent inner jaw of the pin clamp 104. The inner facing side is shown in FIG. 15A and the outer facing side is shown in FIG. 15B. Starting with the inner facing side 270, the saddle 260 includes a centrally disposed through hole 274, a bias member or spring washer seat 276, and a saddle interfacing portion 278 with radial interdigitations 280. The through hole 274 is a central bore extending from the inner facing side 270 to the outer facing side 272. It is sized and configured to receive the stud 108 and is sized to permit the saddle 260 to freely rotate about the stud 108. The spring washer seat 276 and the saddle interfacing portion 278 are concentrically disposed about the through hole 274. As shown in FIG. 15A, the spring washer seat 276 is an indentation sized to receive a portion of the spring washer 268b when the spring washer 268b is in a compressed condition. The saddle interfacing portion 278 is disposed between the spring washer seat 276 and the saddle perimeter and is configured to selectively engage with and provide positive retention from planar rotation when the faces are clamped together, thereby preventing relative rotation between the first and second saddles 260a, 260b when the clamping device 100 is in a fully locked condition or when used with embodiments without an opposing clamp that selectively engage with and prevent relative rotation with some other foundation. In this example, the saddle interfacing portion 278 includes the radial interdigitations or splines that engage corresponding radial interdigitations on the opposing second saddle 260b when the clamping device 100 is fully locked. It is worth noting that the spring washer 268b is disposed between the first and second saddles 260a, 260b. When the clamping device 100 is an unlocked or provisionally locked condition, the first and second saddles 260a, 260b are biased apart by the spring washer 268b. As such, the first and second saddles 260a, 260b can rotate relative to each other. However, when placed in a locked condition, the spring washer 268b compresses within the spring washer seat 276 and the opposing radial interdigitations engage, preventing further relative rotation.

The outer facing side 272 includes a bias member seat or spring washer seat 284, a spacer seat 286 configured to receive one of the thru spacer 264 and the hex spacer 266, and a clamp interfacing portion 288.

The spring washer seat 284 is concentrically disposed about the through hole 274. As shown in FIG. 15B, the spring washer seat 284 is an indentation sized to receive a portion of a spring washer 268a when the spring washer 268a is in a compressed condition. The spacer seat 286 is a non-circular shaped recess that prevents relative rotation between the saddle 260 and the corresponding spacer in the spacer seat 286. In this example the spacer seat 286 includes a main portion 290 and two peripheral wings 292 that extend from the main portion 290. As will become apparent further below, a spring washer in the spacer seat 286 biases the spacer in the spacer seat 286 to an offset or displaced condition when the clamp 100 is in an unlocked or provisionally locked condition.

The clamp interfacing portion 288 is disposed between the spacer seat 286 and the saddle perimeter and is configured to selectively engage with and prevent relative pivoting between the saddle 260 and the pin clamp 104 when the clamping device 100 is in a fully locked condition. As such, the clamp interfacing portion 288 includes a concave saddle portion 294 having about or substantially the same radius as the cylindrical portion of the inner jaw 116. In this example, the concave saddle portion 294 includes linear splines 296 that are shaped to engage corresponding linear splines on the inner jaw 116 of the pin clamp 104 when the clamping device 100 is in a fully locked condition. It is understood that the saddle 260b corresponds to and interfaces with the rod clamp 104.

The thru spacer 264 is shown in FIG. 16. It includes a clamp facing side 302 and a saddle facing side 304. The saddle facing side 304 in FIG. 4 is disposed within the spacer seat 286 and interfaces with the spring washer 268a, while the clamp facing side 302 is arranged to face the adjacent inner jaw 116 of the pin clamp 104. The saddle facing side 304 is a flat surface with a through hole 306 that extends from the saddle facing side 304 through the jaw facing side 304. The through hole 306 is sized and shaped to permit the thru spacer 264 to rotate with its corresponding saddle 260a about the stud 108. The clamp facing side 302 includes a main body 308 and flanges 310 extending on opposing sides of the main body 308. The flanges 310 are shaped and configured to sit within the wings 292 of the spacer seat 286 to prevent relative rotation between the thru spacer 264 and the saddle 260a. The main body 308 includes a height substantially greater than the flanges 310 that projects out from and above the spacer seat 286. The top of the main body 308 includes a smooth cylindrical surface 312. In use, the smooth cylindrical surface 312 concentrically mates with the cylindrical articulating surface 140 of the inner jaw 116. The height of the main body 308 is selected to cooperate with the depth of the saddle assembly receiving area 130 in the outer clamp face 126 to selectively engage and disengage the linear splines of the saddle 260 with the linear splines on the outer clamp face 126 of the inner jaw 116. Particularly, when the spring washer 268a is in an uncompressed state, the thru spacer 264 is offset from the saddle 206. This offset correspondingly offsets the inner jaw 116 from the saddle 206a so that the linear splines of the saddle 260a and the inner jaw 116 are disengaged. In this condition, the inner jaw 116, and thus the entire pin clamp 104, may pivot about the pitch axis 30 relative to the saddle assembly 106, with the cylindrical articulating surface 140 of the inner jaw 116 interfacing with the cylindrical surface 312 on the main body 308 of the thru spacer 264. When the clamp system 100 is placed in the fully locked condition, the spring washer 268a compresses, the offset is reduced or eliminated, and the thru spacer 264 seats more completely or fully within the spacer seat 286. Likewise, the inner jaw 116 moves closer to the saddle 206 until the linear splines on the cylindrical surface of the inner jaw 116 engage the linear splines 296 on the cylindrical concave saddle portion 294 of the saddle 206. This locks the clamp 104 to the saddle assembly 106, preventing further pivoting rotation about the axis.

The hex spacer 266 is shown in FIGS. 17A and 17B. It includes many of the same features of the thru spacer 264 just discussed. Those will not be repeated here, and the discussion above is relied for support of the hex spacer 266. The hex spacer 266 however, includes some additional differences that will be described. The hex spacer 266 includes a saddle facing side 320 and a clamp facing side 326. The saddle facing side includes a boss 322 extending therefrom. The boss 322 is sized to fit through the through hole 274 of the saddle 206. A through hole 324 extends through the boss 322 to the clamp facing surface side 326. The through hole 324 has inner surface features that correspond with outer surface features on the stud 108 to prevent relative rotation between the hex spacer 266 and the stud 108. In this example, the inner surface features are a hex shape formed on the through hole 324, and they extend the length of the through hole 324.

The hex spacer 266 interfaces with the rod clamp 102 in the same manner that the thru spacer 264 interfaces with the pin clamp 104 discussed above. In addition, because the hex spacer 266 does not rotate relative the stud 108, its corresponding saddle and the rod clamp 102 also do not rotate relative to the stud 108. By rotationally fixing at least one of the clamps 102, 104 relative to the stud 108, either of the nuts 112 can be rotated relative to the stud with little fear of the stud 108 rotating relative to the entire clamp assembly. This enables the clamping device 100 to be locked to the final lock state by turning only one of the two nuts 112 shown in FIG. 4.

In use, a surgeon may place the clamping device 100 in the open position by grasping the latch 120 between his thumb and forefinger and translating the latch 120 rearwardly, overcoming the force of the biasing element 133. Once sufficiently drawn back, the biasing springs 114 bias the outer jaw 118 to pivot about the spherical washer 110 to an open position, separating the clamping side of the inner and outer jaws 116, 118 to form an opening having a width, in at least in one embodiment, greater than a width of the fixation element to be inserted therein.

When a fixation element is introduced to the clamps 102, 104 through the opening and against the outer jaw, the outer jaw is forced rearwardly and forced to rotate about the spherical washer 110. As this occurs, the catch surfaces 172, 328 on the outer jaw rise above the lock close interface 228 on the latch 120. As this occurs, the latch 120 moves under spring force toward the clamp side to prevent the jaws from opening back up. In addition to having the lock close interface 228 moving between the inner and outer jaws 116, 118, the leading tip 216 of the forward portion 208 of the latch 120 engages the catch surfaces 177, 326 on the lateral shoulders of the outer jaw. Since the latch 120 is also fixed within a latch race formed in the inner jaw, the latch 120 is effectively capturing the inner and outer jaws and preventing the jaws from opening.

With the fixation element captured between the jaws, the clamping device 100 is in a provisionally locked condition. That is, the fixation element is provisionally secured within the clamp between the outer and inner jaws. In this position, the fixation element may be rotated within the clamp or the clamp may be rotated about the fixation element, the clamp may be slid along the fixation element, and the inner and outer jaws 116, 118 may be pivoted relative to the saddle assembly 106 and rotated about the stud 108. Thus, the clamp captures a fixation element but permits continued adjustment as the surgeon finishes locating the pins or building the frame.

Once the pins and bars are in a desired position, and with reference to FIG. 4, the surgeon locks the clamping device 100 against further movement by tightening one or both of the nuts 112 on the stud 108. As discussed above, by virtue of the hex spacer 266 preventing rotation of the bar clamp relative to the stud 108, tightening only one nut can place the clamping device in the final locked state. As the nut is tightened, the spring washers 268 compress in the saddle assembly 106. As the spring washer 268b between the saddles 260a, 260b compresses, the interdigitations on the saddles provide positive retention from planar rotation. In addition, the spring washers 268a, 268c separating the saddles 260a, 260b and the spacers 264, 266 compress, the splines on the inner jaws engage the splines on the concave side of the saddles 260a, 260b, and the spherical washer 110 tightens against the outer jaw 118. The outer jaw 110 then is forced against the fixation element and the latch 120 to more tightly secure the fixation element in place between the jaws. Thus, in a fully locked state, the clamping device 100 is locked against all relative movement of the clamps, including releasing the fixation element.

To release the bar, the surgeon performs the steps in reverse. Particularly, he first loosens one or both of the nuts 112, placing the clamping device 100 in the provisionally locked state. Then he may grasp and pull the latch 120 so that the cross bar 206 moves out from between the inner and outer jaws and so that the leading tip 216 moves from its position above the catch surface on the lateral shoulder. The jaws will then separate opening the clamp, and the bar may be removed.

Figure 18:
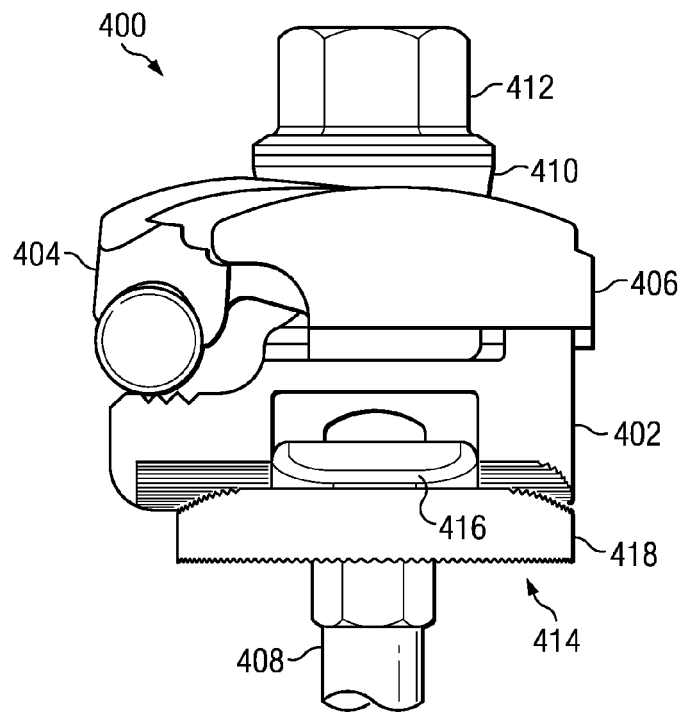
FIG. 18 is an illustration of a plan view of an exemplary clamp of an alternative clamping device in accordance with one exemplary aspect of the present disclosure.

FIG. 18 shows another embodiment of a portion of a clamping device. Here, only a single clamp is shown, referenced herein by the reference numeral 400. Although only a single clamp is shown, some embodiments include a second clamp secured thereto in the manner discussed above so that the clamping device 400 includes two clamp systems. Other embodiments include a separate foundation or base that that provides stability in some other way.

This clamp 400 is configured much like the clamping device 102 discussed above, and includes an inner jaw 402, an outer jaw 404, a latch 406, a stud 408, a spherical washer 410, and a nut 412. Here, a portion of a saddle assembly 414 is shown, with a spacer 416 and a saddle 418. A fixation element as a bar or pin is shown in place between the inner and outer jaws 402, 404. As discussed above, in some embodiments, the fixation elements need not be fully between the jaws to be considered between the jaws.

Much of the discussion above apples equally to the clamp 400, and will not be repeated in detail here. The difference between the clamp 400 and the pin claim 104 disclosed above becomes apparent with a discussion of the outer jaw 404 and the latch 40.

Figure 19:
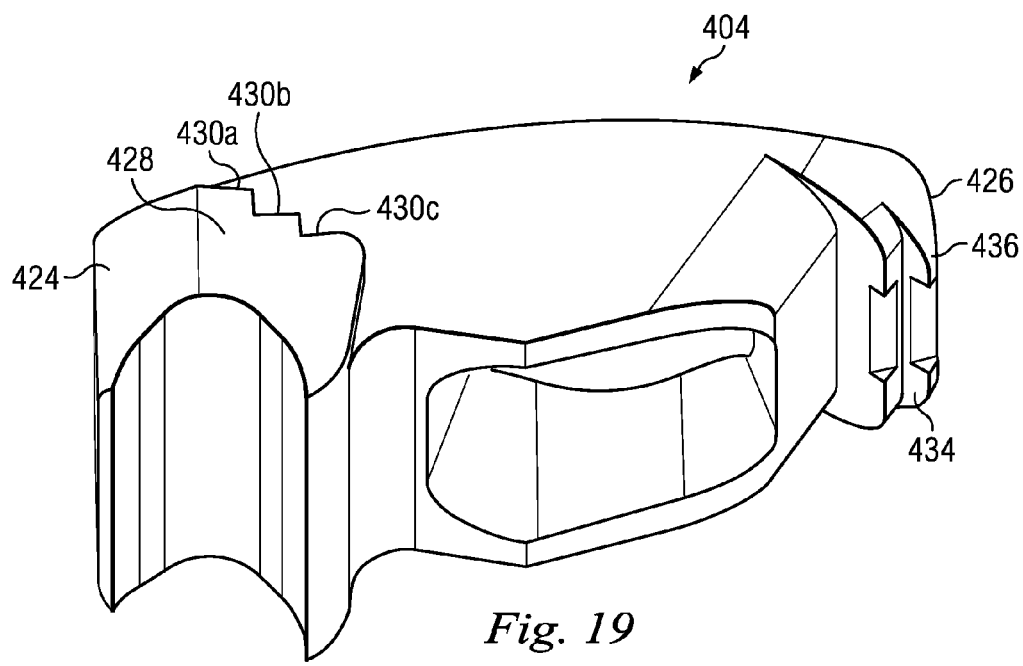
FIG. 19 is an illustration of an exemplary outer jaw of the clamp of FIG. 18 in accordance with one exemplary aspect of the present disclosure.
Figure 20:
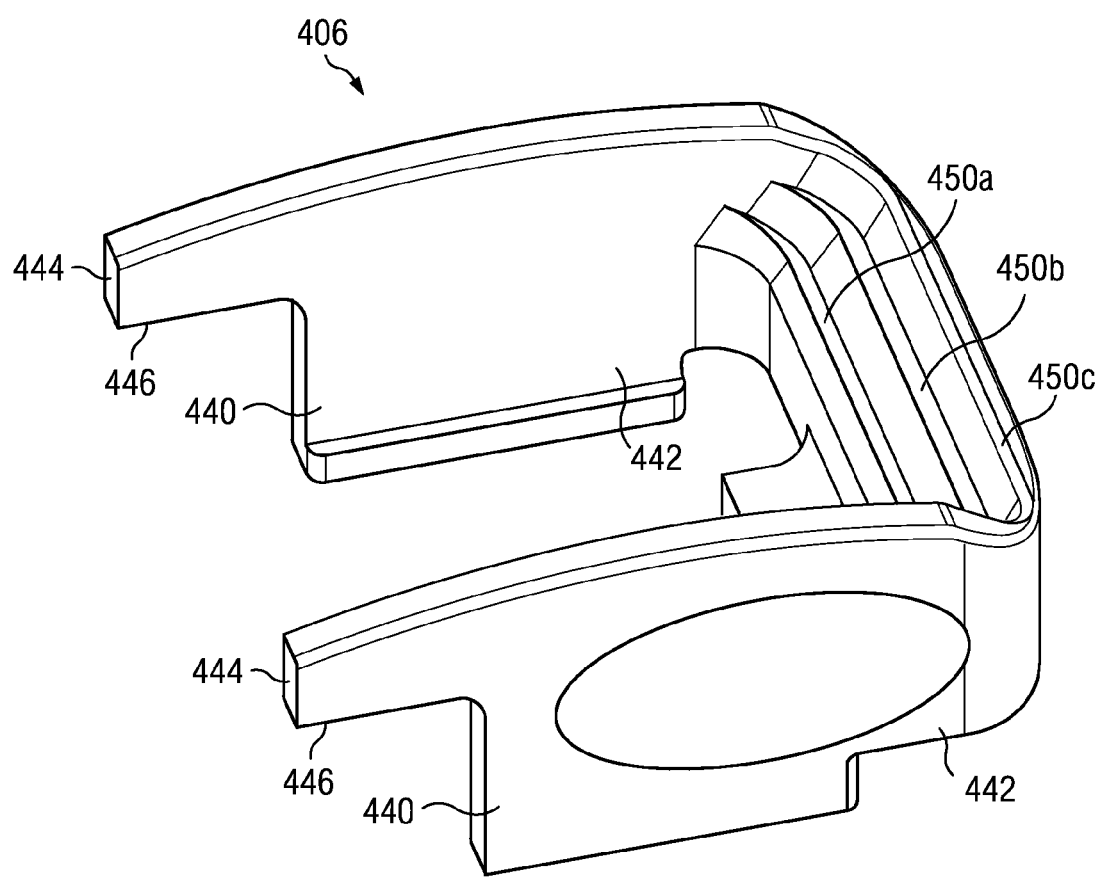
FIG. 20 is an illustration of an exemplary latch of the clamp of FIG. 18 in accordance with one exemplary aspect of the present disclosure.

FIG. 19 shows the outer jaw 404, and FIG. 20 shows the latch 406. The outer jaw 404 includes a clamping end 424 and a rearward end 426. The clamping end 424 includes lateral shoulders 428 with catch surfaces 430a-c formed therein. The rearward end 426 includes a lock close interface 434 and a lock open interface 436.

FIG. 20 shows the latch 406. It includes a forward end 440 and a rearward end 442. The forward end 440 includes a leading tip 444 having an engagement surface 446. The rearward end 442 includes a series of engagement surfaces formed as an array or series of steps or ridges, referred to herein as catch surfaces 450.

Accordingly, the clamp 400 includes two locking arrangements that positively engage to prevent separation of the inner and outer jaws 402, 404. The first is formed of catch surfaces 424 on lateral shoulders 426 of the upper jaw 404, similar to that discussed above. The second is formed at the rearward end of the upper jaw 404 and the latch 406 with the catch surfaces 450, like that discussed above, however the catch surfaces are disposed on the latch 406 instead of the upper jaw.

Figure 24:
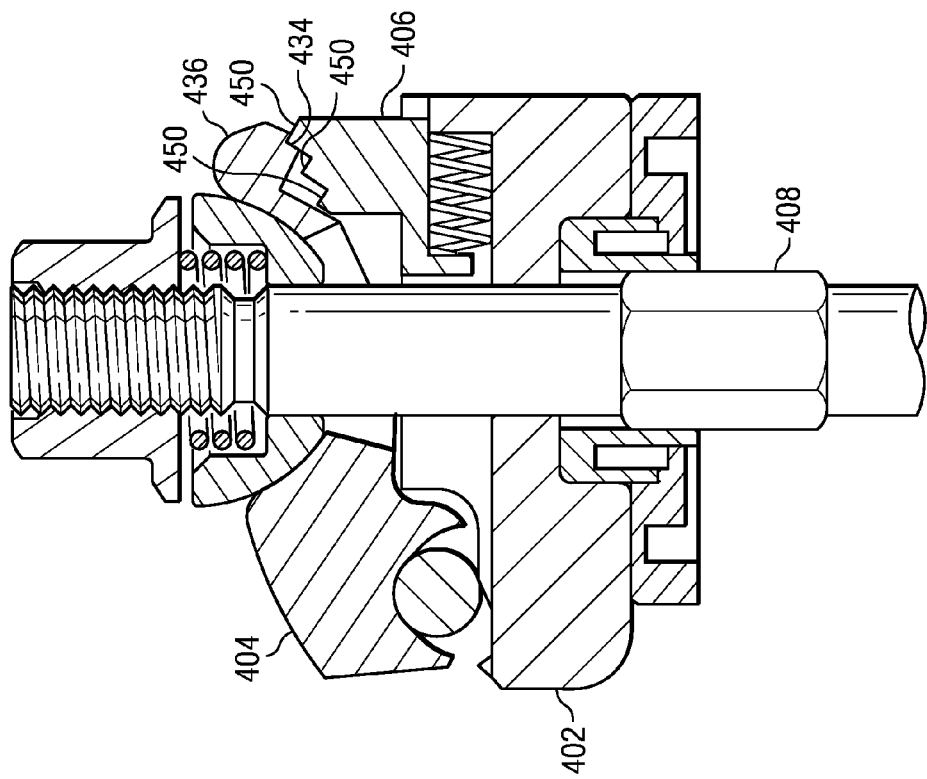
FIG. 24 is an illustration of a cross-sectional view of the clamp of FIG. 18 in a third locking condition for a third sized fixation element.
Figure 23:
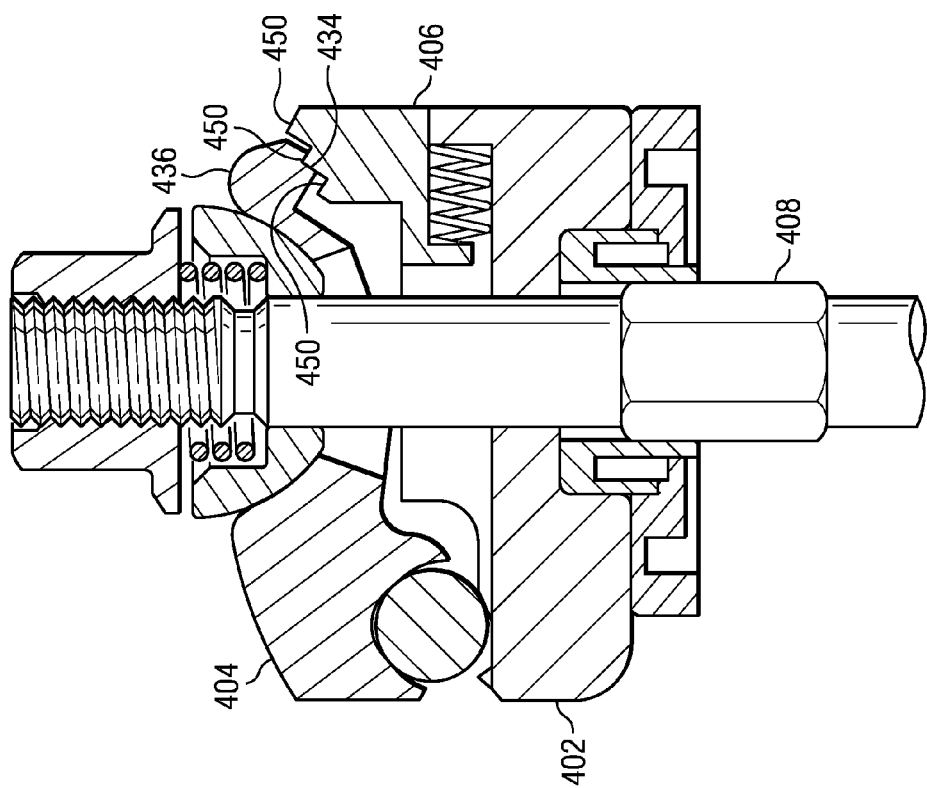
FIG. 23 is an illustration of a cross-sectional view of the clamp of FIG. 18 in a second locking condition for a second sized fixation element.

FIGS. 21-24 show the device in cross-section displaying the catch surfaces 450 on the latch 406 interacting with the surfaces on the outer jaw 404 for various sized fixation elements. FIG. 21 shows the clamp 400 with the latch 406 pulled out of the way so that the clamp 400 can be opened. FIG. 22 shows the locking arrangement on a relatively larger fixation element, such as a 6 mm pin. FIG. 23 shows the locking arrangement on a relatively medium sized fixation element, such as a 5 mm pin. FIG. 24 shows the locking arrangement on a relatively smaller fixation element, such as a 4 mm pin. It should be noted that many rods and other fixation elements having a much larger diameter than the exemplary pins discussed herein. The clamp may be adjusted to compensate for these sizes based on the principles disclosed herein.

One embodiment of the current disclosure includes multiple steps in the top jaw such that depending upon how far the jaw slides, the space between the inner and outer jaws will be sized to fit with a selected particular size of bars or pins. The extension of this embodiment is to utilize an angled surface so that nearly any size bar or pin can be held. At larger angles, it is possible that the force of the bar acting to open the top jaw may be greater than the force of friction preventing opening. Utilizing friction enhancing features can increase the angle of the surface, decreasing the required sliding distance of the top jaw. Mother embodiment of this invention provides multiple slider locations for the top jaw relative to the bottom jaw so that the top jaw can be mobilized along a direction that locks a particular shape. By changing the track which the top jaw slides, different size bars or pins can be locked. A third embodiment of this invention utilizes multiple latches that change the space between the inner and outer jaws. Other embodiments can incorporate two of the above embodiments, or even all three, into one device.

The systems, devices, and methods disclosed herein enable users to build and implement an external fixation system for the treatment of bone conditions. Because of the advantages disclosed herein, a user may be able to insert and secure fixation elements of different sizes into a provisional locking arrangement, where the fixation element cannot be inadvertently or prematurely removed without a step of actuating a latch. The locking mechanism disclosed herein, using first and second locking arrangements, permits a user to use a wedge between the jaws to actively limit the range of relative pivoting of the plates or to use a latch that captures a part of each of the upper and lower jaws between latch elements to positively retain the jaws in the provisionally locked condition. As discussed above, either locking arrangement may be used in clamping devices independent of the other.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

We claim:

1. A clamping device for selectively attaching to external fixation elements having different cross-sectional sizes, comprising:
  a first jaw having an inner surface and an outer surface;
  a second jaw having an inner surface and an outer surface, the inner surface of the first jaw and the inner surface of the second jaw together forming a passage configured to receive the external fixation elements having different cross-sectional sizes; and
  a locking system engageable with the first and the second jaws, a portion of the locking system being moveable laterally relative to the first and the second jaws between a receiving position, a first locking position, and a second locking position, wherein:

in the receiving position, the locking system permits the first and second jaws to separate to receive an external fixation element;

in the first locking position, the locking system is configured to limit separation of the first and second jaws to a first amount in a manner that prevents release of an external fixation element having a first size from between the first jaw and the second jaw;

in the second locking position, the locking system is configured to limit separation of the first and second jaws to a second amount in a manner that prevents release of an external fixation element having a second size from between the first jaw and the second jaw;

the first jaw comprises a first engagement surface and a second engagement surface, said moveable portion of the locking system comprising a third engagement surface disposed to selectively engage one of the first and second engagement surfaces on the first jaw; and the first and second engagement surfaces of the first jaw face away from the second jaw.

2. The clamping device of claim 1, wherein said moveable portion of the locking system comprises a wedge configured for selective disposal between the first and the second jaws.

3. The clamping device of claim 1, wherein the clamping device comprises a clamping side and a rearward side, the first engagement surface and the second engagement surface being disposed at the rearward side.

4. The clamping device of claim 1, wherein the clamping device comprises a clamping side and a rearward side, the first engagement surface and the second engagement surface being disposed at the clamping side.

5. The clamping device of claim 1, wherein the locking system is biased to a provisionally locking condition.

6. The clamping device of claim 1, wherein the locking system is configured to provisionally lock a 5 mm rod and configured to provisionally lock a 6 mm rod.

7. A clamping device for selectively attaching to external fixation elements having different cross-sectional sizes, comprising:
a first jaw having an inner surface and an outer surface;
a second jaw having an inner surface and an outer surface, the inner surface of the first jaw and the inner surface of the second jaw together forming a passage configured to receive the external fixation elements having different cross-sectional sizes; and
a locking system moveable laterally relative to the first jaw and the second jaw and configured to selectively adjust separation of the first jaw and the second jaw between a receiving position, a first locking position, and a second locking position, the locking system comprising:
a first locking arrangement configured to correspond to the first locking position for a fixation element having a first size, the first locking arrangement being configured to limit separation of the first and second jaws to a first amount in a manner that prevents release of the fixation element having the first size from between the first jaw and the second jaw, and
a second locking arrangement configured to correspond to the first locking position for a fixation element having a second size, the second locking arrangement being configured to limit separation of the first and second jaws to a second amount in a manner that prevents release of the fixation element having the second size from between the first jaw and the second jaw, the first locking arrangement being different than the second locking arrangement and the first size being different than the second size, the first jaw comprising a first engagement surface and a second engagement surface, the locking system comprising a third engagement surface disposed to selectively engage one of the first and second engagement surfaces on the first jaw; and the first and second engagement surfaces of the first jaw facing away from the second jaw.

8. The clamping device of claim 7, wherein the first locking arrangement comprises the first engagement surface and the second locking arrangement comprises the second engagement surface, the first engagement surface having an elevation different than the second engagement surface.

9. The clamping device of claim 8, wherein the first engagement surface and the second engagement surface are formed on lateral sides of the first jaw.

10. The clamping device of claim 7, wherein the first and second locking arrangements comprise a common latch mechanism movable between a first position where the latch mechanism forms a part of the first locking arrangement to a second position where the latch mechanism forms a part of the second locking arrangement.

11. The clamping device of claim 10, wherein the latch mechanism includes a portion extending between the first and second jaws to obstruct relative pivoting motion of the first and second jaws.

12. The clamping device of claim 7, wherein the first locking arrangement comprises the first engagement surface and the second locking arrangement comprises the second engagement surface, and wherein the first and second locking arrangements comprise a common latch mechanism movable between a first position where the latch mechanism engages the first engagement surface and a second position where the latch mechanism engages the second engagement surface.

13. The clamping device of claim 12, wherein the first and second engagement surfaces are steps laterally and elevationally offset from each other.

14. A clamping device for an external fixation system, comprising:
a first clamping system, a second clamping system, and a post component extending into the first and second clamping system;
the first clamping system for selectively attaching to external fixation elements having different cross-sectional sizes, the first clamping system comprising:
a first outer jaw;
a first inner jaw having an inner surface facing the outer jaw, the outer and inner jaws together forming a passage for receiving fixation elements having different cross-sectional sizes; and
a locking system engageable with the first outer and the first inner jaws, a portion of the locking system being moveable laterally relative to the first outer and the first inner jaws between a receiving position, a first locking position, and a second locking position, wherein:
in the receiving position, the locking system permits the first outer and the first inner jaws to separate to receive an external fixation element;
in the first locking position, the locking system is configured to limit separation of the first outer and the first inner jaws to a first amount in a manner that prevents release of an external fixation element having a first size from between the first outer and the first inner jaws; and in the second locking position, the locking system is configured to limit separation of the first outer and the first inner jaws to a second amount in a manner that prevents release of an external fixation element having a second size from between the first outer and the first inner jaws; and the second clamping system comprising:
   a second outer jaw; and
   a second inner jaw having an inner surface facing the second outer jaw, the second outer and second inner jaws together forming a second opening for receiving a second fixation element of the external fixation system.

15. The clamping device of claim 14, further comprising a saddle assembly disposed between the first and the second clamping systems.

16. The clamping device of claim 15, wherein the first inner jaw includes a substantially cylindrical outer surface portion having splines formed thereon, and
   wherein the saddle assembly comprises a concave surface including splines thereon, the splines of the first inner jaw interdigitating with the splines of the saddle assembly.

* * * * *